United States Patent
Rhodes et al.

(10) Patent No.: US 12,038,429 B2
(45) Date of Patent: Jul. 16, 2024

(54) DETECTION OF DRUG RESISTANCE OF MICROORGANISMS

(71) Applicant: Specific Technologies, LLC, West Palm Beach, FL (US)

(72) Inventors: Paul A. Rhodes, Woodside, CA (US); Soumitesh Chakravorty, Sunnyvale, CA (US); Sung Hyun Lim, Mountain View, CA (US)

(73) Assignee: Specific Diagnostics, LLC, San Jose, CA (US)

( * ) Notice: Subject to any disclaimer, the term of this patent is extended or adjusted under 35 U.S.C. 154(b) by 149 days.

(21) Appl. No.: 15/907,695

(22) Filed: Feb. 28, 2018

(65) Prior Publication Data

US 2018/0252701 A1     Sep. 6, 2018

Related U.S. Application Data

(60) Provisional application No. 62/465,691, filed on Mar. 1, 2017.

(51) Int. Cl.
*G01N 33/50* (2006.01)
*C12Q 1/02* (2006.01)
(Continued)

(52) U.S. Cl.
CPC ......... *G01N 33/5008* (2013.01); *C12Q 1/025* (2013.01); *C12Q 1/04* (2013.01);
(Continued)

(58) Field of Classification Search
CPC .... G01N 33/5008; G01N 21/78; G01N 21/03; G01N 21/80; G01N 2201/0446;
(Continued)

(56) References Cited

U.S. PATENT DOCUMENTS 4,118,280 A    10/1978  Charles
4,252,904 A    2/1981   Nelson
(Continued)

FOREIGN PATENT DOCUMENTS

WO    2013/163610 A1    10/2013
WO    2018/152372 A1    8/2018

OTHER PUBLICATIONS

Pavan et al. "Loss of susceptibility as a novel breeding strategy for durable and broad-spectrum resistance" Mol Breeding (2010) 25:1-12 (Year: 2010).*

(Continued)

*Primary Examiner* — Blaine Lankford
*Assistant Examiner* — Lauren K Van Buren

(57) ABSTRACT

Devices, systems, and methods for strain-specific identification and assessment of susceptibility of microorganisms based on the response of sensors in a colorimetric sensor array to metabolic products of the microorganism. An exemplary method includes culturing a sample containing microorganisms in a medium and in gaseous communication with a colorimetric sensor array. Sensors in the colorimetric sensor array are exposed to volatile organic compounds produced by the microorganism. The method then includes assessing a resistance of the microorganism to at least one substance. The resistance is assessed based on a response of the sensors in the colorimetric sensor array to the volatile organic compounds produced by the microorganism.

17 Claims, 16 Drawing Sheets

(51) Int. Cl.
    *C12Q 1/04*       (2006.01)
    *C12Q 1/18*       (2006.01)
    *C12Q 3/00*       (2006.01)
    *G01N 21/03*     (2006.01)
    *G01N 21/78*     (2006.01)
    *G01N 21/01*     (2006.01)
    *G01N 21/80*     (2006.01)

(52) U.S. Cl.
    CPC ............... *C12Q 1/18* (2013.01); *C12Q 3/00* (2013.01); *G01N 21/03* (2013.01); *G01N 21/78* (2013.01); *G01N 2021/0118* (2013.01); *G01N 21/80* (2013.01); *G01N 2201/0446* (2013.01)

(58) Field of Classification Search
    CPC .... G01N 2021/0118; C12Q 1/18; C12Q 1/04; C12Q 3/00; C12Q 1/025
    See application file for complete search history.

(56) References Cited

U.S. PATENT DOCUMENTS

| | | | |
|---|---|---|---|
| 5,232,839 A | 8/1993 | Eden | |
| 5,996,586 A | 12/1999 | Phillips | |
| 6,190,858 B1 | 2/2001 | Persuad et al. | |
| 6,312,390 B1 | 11/2001 | Phillips | |
| 6,368,558 B1 | 4/2002 | Suslick et al. | |
| 6,620,107 B2 | 9/2003 | Payne et al. | |
| 6,627,394 B2 | 9/2003 | Kritzman et al. | |
| 6,841,391 B2 | 1/2005 | Lewis et al. | |
| 6,903,823 B1 | 6/2005 | Muller | |
| 8,852,504 B2 | 10/2014 | Suslick et al. | |
| 10,837,044 B2 | 11/2020 | Rolain et al. | |
| 2002/0119513 A1* | 8/2002 | Alocilja | G01N 33/0031 435/287.5 |
| 2009/0239252 A1 | 9/2009 | Trevejo et al. | |
| 2010/0291617 A1 | 11/2010 | Treveho et al. | |
| 2015/0009969 A1 | 1/2015 | Ishizu | |
| 2015/0099694 A1* | 4/2015 | Lim | G16B 35/00 514/2.7 |

OTHER PUBLICATIONS

Wright et al. "Bacteria resistance to antibiotics: Enzymatic degradation and modification" Advanced Drug Delivery Reviews 57 (2005) 1451-1470. (Year: 2005).*
Guo "Fluorescence chemosensors for hydrogen sulfide detectin in biological systems" Analyst. 2015, 140, 1772-1786. (Year: 2015).*
Carey et al. "Rapid Identification of Bacteria with a Disposable Colorimetric Sensing Array" J Am Chem Soc. May 18, 2011: 133(19) : 7571-7576 (Year: 2011).*
Feng et al.; "A Simple and Highly Sensitive Colormetric Detection Method for Gaseous Formaldehyde", J. Am. Chem. Soc., vol. 132, p. 4046-4047, (2010).
Suslick et al., "Discrimination of Complex Mixtures by a Colorimetric Sensor Array: Coffee Aromas". Anal Chemistry, vol. 82, No. 5, pp. 2067-2073, (2010).
Feng et al.; "A colorimetric sensor array for indentification of toxic gases below permissible exposure limits", Chem. Communication, vol. 46, pp. 2037-2039, (2010).
Rakow et al. "A colorimetric sensor array for odour visualization", Nature, vol. 406, pp. 710-713, (2000).
Lim et al.; "A colorimetric sensor array for porous pigments", Analyst, vol. 134, pp. 2453-2457, (2009).
Lim et al.; "An optoelectronic nose for the detection of toxic gases", Nature Chemistry, vol. 1, pp. 562-567, (2009).
"Antimicrobial treatment guidelines for acute bacterial rhinosinusitis", Otolarygology-Head and Neck Surgery, vol. 130, No. 1, pp. 1-45, (2004).
Zechman et al. "Characterzation of Pathogenic Bacteria by Automated Headspace Conventration-Gas Chromatography", Journal of Chromatography, vol. 377, pp. 49-57, (1986).
Suslick et al., "Colorimetric sensor arrays for molecular recognition", Tetrahedron, vol. 60, pp. 11133-11138, (2004).
Gwaltney et al., "Computed Tomographic Study of the Common Cold", The New England Journal of Medicine, vol. 330, No. 1, pp. 25-30, (1994).
Kaur-Atwal et al.; "Chemical standardd for ion mobility spectrometry: a review", Int. J. Ion Mobil. Spec., vol. 12, pp. 1-14, (2009).
Thaler et al., "Diagnosis of rhinosinusitis with a colorimetric sendor array", J. Breath Res. vol. 2, pp. 1-4, (2008).
Suslick et al., "Discrimination of Complex Mixtures by a Colorimetric Sensor Array: Coffee Aromas".Department of Chemistry, Univ. of Ill. pp. 1-21.
Lai et al., "Identification of Upper Respiratory Bacterial Pathogens with the Electronic Nose", Laryngoscope, vol. 112, pp. 975-979, (2002).
Cherry et al., "National Ambulatory Medical Care Survey:2006 Summary", National Health Statistics Reports, No. 3, pp. 1-40, (2008).
Dosh et al., "Predictors of Antibiotic Prescribing for Nonspecific Upper Respiratory Infections, Acute Bronchits, and Acute Sinusitis", The Journal of Family Practice, vol. 49, No. 5. pp. 407-414, (2000).
Hamilton-Kemp et al., "Production of the Long-Chain Alcohols Octanol, Decanol, and Dodecanol by *Escherichia coli*", Current Microbiology, vol. 51, pp. 82-86, (2005).
Cary et al., "Rapid Identification of Bacteria with a disposable Colorimetric Sensing Array", Journal of American Chemical Society, pp. A-F, (2011).
Suslick et al., "Seeing Smells: Development of an Optoelectronic Nose", Quim, Noca, vol. 30, No. 3, pp. 677-681, (2007).
Scotter et al., "The rapid evaluation of bacterial growth in blood cultures by selected ion flow tube-mass spectrometry (SIFT-MS) and comparison with BacT/ALERT automated blood culture system", Journal of Microbiological Methods, vol. 65, pp. 628-631, (2006).
Sharp et al., "Treatment of Acute and Chronic Rhinosinusitis in the United States, 1999-2002", Arch Otolaryngol Head Neck Surg., No. 133, pp. 260-265, (2007).
Preti et al., "Volitale compounds characteristic of sinus-related bacteria and infected sinus mucus: Analysis by solid-phase microextraction and gas chromatography-mass spectrometry", Journal of Chromatography B, vol. 877, pp. 2011-2018, (2009).
Zechman et al., "Volatiles of Pseudomonas aeruginosa and related species by automated headspace concentration—gas chromatography", Can. J. Microbiol. vol. 31, pp. 232-237, (1985).
Brenner et al., "Computed Tomography—An Increasing Source of Radiation Exposure", The New England Journal of Medicine, vol. 357, No. 22, pp. 2277-2284, (2007).
Munita et al. "Mechanisms of Antibiotic Resistance," Microbial Spectrum, Apr. 8, 2016 5, 7-10 (Apr. 8, 2016), vol. 4, Iss. 2, pp. 1-37.
Lonsdale, C. L. et al., "The Use of Colorimetric Sensor Arrays to Discriminate between Pathogenic Bacteria," PLOS ONE, 8(5): e2726, May 9, 2013.
Kadlek, M. W. et al., "A Cell Phone-Based Microphotometric System for Rapid Antimicrobial Susceptibility Testing" Journal of Laboratory Automation Society for Laboratory Automation and Screening, pp. 258-266, Dec. 31, 2014.
Extended European Search Report in European Patent Application No. EP 18760618.1, mailed Mar. 19, 2021 (9 pages).
Gordon, N.C., et al., "Prediction of *Staphylococcus aureaus* Antimicrobial Resistance by Whole-Genome Sequencing", Journal of Clinical Microbiology, vol. 52, No. 4, Apr. 1, 2014, pp. 1182-1191, XP09324556, US.
European Search Report in European Patent Application No. EP 22212291, dated Feb. 16, 2023 (5 pages).

\* cited by examiner

DETECTION OF DRUG RESISTANCE OF MICROORGANISMS

CROSS-REFERENCE TO RELATED APPLICATIONS

This application claims priority to and the benefit of U.S. Provisional Patent Application No. 62/465,691, filed Mar. 1, 2017 and entitled "Detection of Drug Resistance of Microorganisms," the contents of which are hereby incorporated by reference in their entirety as if fully set forth herein.

FIELD OF THE INVENTION

This disclosure is related to determining an antibiotic susceptibility or resistance of microorganisms.

BACKGROUND

Antibiotic resistance has now become a global threat for healthcare systems. In the U.S., the Center for Disease Control and Prevention (CDC) has recently estimated 2 million patients per year are directly affected by antibiotic-resistant pathogens, leading to more than 23,000 deaths. In addition, the health care costs related to antibiotic resistance are steadily increasing, already exceeding costs of more than $20 billion annually; with the inclusion of lost productivity, the total cost exceeds $35 billion. Despite the increasing concerns, currently available methods are time-consuming and require significant technical expertise. Conventional antimicrobial susceptibility testing (AST) includes disk diffusion, agar dilution, antibiotic gradient disks, and broth microdilution testing, which is the current reference standard. Sepsis is initially diagnosed from clinical signs and symptoms such as otherwise unexplained body temperature alterations (hyperthermia or hypothermia), tachycardia, tachypnea, peripheral vasodilation, or shock. The clinical diagnosis typically triggers a wide spectrum of powerful antibiotic treatments that may or may not be appropriate to the specific infection, which is identified by a subsequent blood culture. Inappropriate antibiotic therapy doubles sepsis-induced mortality, which increases every hour from the onset of septic shock until the delivery of an effective antibiotic. Therefore, the faster a causative organism is identified, the better the patient outcome.

Antibiotic susceptibility is typically determined in a three-day process that includes an average two-day plate growth phase (as the initial concentrations in blood of microorganisms may be on the order of 3 or 5 CFU/ml) followed by a susceptibility test in an automatic scanner. In some cases, effective antibiotic treatment of a patient may not begin until susceptibility is assessed. Thus, reducing the amount of time required to assess antibiotic susceptibility would be advantageous.

One of the earliest antimicrobial susceptibility testing methods was the macrobroth or tube-dilution method [1]. This procedure involved preparing two-fold dilutions of antibiotics (eg, 1, 2, 4, 8, and 16 µg/mL) in a liquid growth medium dispensed in test tubes [1, 2]. The antibiotic-containing tubes were inoculated with a standardized bacterial suspension of 1-5×105 CFU/mL. Following overnight incubation at 35° C., the tubes were examined for visible bacterial growth as evidenced by turbidity. The lowest concentration of antibiotic that prevented growth represented the minimal inhibitory concentration (MIC). The precision of this method was considered to be plus or minus 1 two-fold concentration, due in large part to the practice of manually preparing serial dilutions of the antibiotics [3]. The advantage of this technique was the generation of a quantitative result (ie, the MIC). The principal disadvantages of the macrodilution method were the tedious, manual task of preparing the antibiotic solutions for each test, the possibility of errors in preparation of the antibiotic solutions, and the relatively large amount of reagents and space required for each test.

Presently, instrument systems are utilized to standardize the reading of end points and produce susceptibility test results. For example, some instruments can incubate and analyze 40-96 microdilution trays. As in the manual method, the instruments monitor the well for turbidity changes to indicate the presence or absence of bacteria.

Accordingly, no other methods presently exist than to directly determine susceptibility by measuring whether organisms will grow and reproduce in the presence of antibiotics. Therefore, the timeline required to determine the susceptibility is relatively long, leading to many cases of death from sepsis that could be avoided if detection is discovered earlier. Antimicrobial resistance is a growing challenge in the care of critically ill patients, among whom the burden of infection remains high. Escalating rates of antibiotic resistance add substantially to the morbidity, mortality, and cost related to infection in the ICU [1]. Traditionally, most efforts to understand issues of resistance and ICU outcomes have addressed Gram-positive organisms, such as methicillin-resistant *Staphylococcus aureus* [2],[3].

However, in the United States, alarming trends in resistance are now also reported for a number of Gram-negative pathogens. For example, extended-spectrum beta-lactamase (ESBL) organisms are now endemic in many ICUs, and 15 to 20% of all *Pseudomonas aeruginosa* isolates from serious infections are categorized as multidrug resistant (MDR) because of reduced in vitro susceptibility to three or more classes of antibiotics [4]-[6]. Of even more concern are pathogens for which clinicians have few antibiotic options, namely *Acinetobacter baumanii* and carbepenemase-producing Enterobacteriaceae (CPE) [4]-[6]. In the case of these Gram-negative organisms, studies also point to an association between resistance and both clinical and economic outcomes.

SUMMARY

Colorimetric sensors can be utilized to determine a susceptibility of a given microorganism, or a sample suspected to contain a microorganism, or an antibiotic. In some aspects, this system could be utilized to identify a type of bacteria or other microorganism (that has infected for example a patient) by culturing a blood sample from the patient or other mammal in the presence of the colorimetric sensor array (CSA). Accordingly, if a patient is suspected to have sepsis, samples of the patient's blood could be tested to determine (1) if the patient has an infection, (2) the identity of the microorganism infecting the patient, and (3) the susceptibility or resistance of that microorganism to the applied antibiotics.

An exemplary embodiment of a methodology according to the present disclosure includes culturing a sample which contains microorganisms in a medium and in gaseous communication with a colorimetric sensor array. Sensors in the colorimetric sensor array are thereby exposed to volatile organic compounds produced by the microorganism in the sample. The method further comprises assessing a resistance of the microorganism to at least one substance based on a response of the sensors in the colorimetric sensor array to the volatile organic compounds produced by the microorganism.

In some implementations, the method can include assessing a mode of resistance of the microorganism to the at least one substance. Assessing this mode of resistance can be based on the response of the sensors in the colorimetric sensor array to the volatile organic compounds produced by the microorganism. The resistance of the microorganism to at least one substance can be a multi-drug resistance or a resistance to a certain antibiotic. The mode of resistance can include any one or a combination of any of the following: an efflux pump, an enzymatic breakdown of the substance, an alteration of the site to which the substance binds, an alteration of a metabolic pathway, or a modification to a cell envelope of the microorganism.

Another exemplary embodiment is related to reducing a population of a selected microorganism in a mammal carrying the microorganism, and includes collecting a sample including at least one of the selected microorganisms from the mammal, culturing the microorganism(s) in the presence of a colorimetric sensor array, thereby exposing sensors in the colorimetric sensor array to volatile organic compounds produced by the microorganism(s), identifying susceptibility of the microorganism(s) to a substance based on the response of the sensors in the colorimetric sensor array to the volatile organic compounds produced by the microorganism(s), and administering a dose of the substance to the mammal, wherein the dose is effective to reduce the population of the identified microorganism in the mammal.

A third exemplary embodiment is related to reducing a bacterial population in a mammal showing symptoms of infection, and includes collecting a sample of bacteria from the mammal, culturing some of the bacteria in the presence of a colorimetric sensor array, thereby exposing sensors in the colorimetric sensor array to volatile organic compounds produced by the bacteria, identifying susceptibility of the bacteria to a substance based on the response of the sensors in the colorimetric sensor array to the volatile organic compounds produced by the bacteria, and administering a dose of the substance to the mammal, wherein the dose is effective to reduce the number of the identified bacteria in the mammal.

A fourth exemplary embodiment includes culturing a sample comprising a species of bacteria in the presence of a colorimetric sensor array, thereby exposing sensors in the colorimetric sensor array to volatile organic compounds produced by the bacteria, and identifying the bacteria by species and strain based on the response of the sensors in the colorimetric sensor array to the volatile organic compounds produced by the bacteria, wherein identifying the bacteria by species and strain comprises identifying a substance-resistant strain of a species of bacteria.

Another exemplary embodiment according to the present disclosure can include culturing a sample that may contain microorganisms in gaseous communication with a colorimetric sensor array. Sensors in the colorimetric sensor array are exposed to volatile organic compounds produced by a microorganism in the sample. The method can then include detecting a response of the colorimetric sensor array to the volatile organic compounds produced by the microorganism. The method can then include determining a resistance of the microorganism to at least one substance based on the detected response of the colorimetric sensor array.

Implementations of the general aspects can include one or more of the following features.

The microorganism can be identified by species and strain (e.g., based on the response of the sensors in the colorimetric sensor array to the volatile organic compounds produced by the bacteria) before identifying the susceptibility of the bacteria to the substance. Identifying the bacteria by species and strain may include identifying an antibiotic-resistant mutant.

The microorganism may be collected from a substrate before culturing the microorganism. The substrate may be, for example, woven or nonwoven fabric, paper, metal, or plastic.

In some cases, the microorganism is collected from a mammal (e.g., a human) before culturing the microorganism. Collecting the microorganism from the mammal may include collecting a fluid sample or a tissue sample from the mammal, wherein the fluid sample comprises a gas (e.g., exhaled breath), a liquid (e.g., blood), or a combination thereof. The mammal may be showing symptoms of bacteremia.

A substance to which the microorganism is susceptible may be identified based on the response of the sensors in the colorimetric sensor array to the volatile organic compounds produced by the microorganism. The substance may be, for example, a medication approved for use by animals or humans. The substance may be selected based on the identified species and strain of the microorganism (e.g., bacteria). In some cases, a dose of the substance is administered to the mammal from which the microorganism was collected, wherein the dose is effective to reduce the number of the identified microorganisms in the mammal.

In some cases, susceptibility of the microorganism to the substance can be assessed within 64 hours, within 48 hours, within 36 hours, within 24 hours, within 12 hours, within 10 hours, within 8 hours, within 6 hours, or within 4 hours after identification of the microorganism.

In certain cases, culturing the bacteria includes culturing the bacteria on a solid medium or in a liquid medium. The response of each sensor may include a change in one or more color components of the sensor or a change of at least one dye on the colorimetric sensor array in a time window. The temporal and/or static response of the sensors may yield a temporal or static color response pattern of the bacteria. Identifying the bacteria by species and strain may include comparing the temporal and/or static color pattern of the bacteria with a library of temporal and/or static color response patterns characteristic of known strains of bacteria.

The response of the colorimetric sensor array can be a response of at least one frequency spectrum of at least one dye on the colorimetric sensor array in a time window. The response of at least one frequency spectrum can be a color response of red, green, or blue. The at least one dye can comprise any one or a combination of any of the following: a dye responsive to reduced sulfur compounds, a redox indicator, or a pH indicator.

Susceptibility or resistance of a bacteria or other microorganism to a substance may be assessed based on the response of the sensors in the colorimetric sensor array to the volatile organic compounds produced by the bacteria. A dose of a substance to which the bacteria is susceptible may be administered to the mammal from which the bacteria was collected, the dose being effective to reduce the number of the identified bacteria in the mammal.

Another exemplary methodology according to the present disclosure can include culturing a sample that may contain microorganisms. The sample can be in communication with a sensor which is sensitive to reduced sulfur compounds. This communication exposes the sensor to volatile organic compounds produced by a microorganism. The method can then include assessing a resistance of the microorganism to at least one substance based on a response of the sensor.

Another exemplary methodology according to the present disclosure can include culturing a sample that contains microorganisms in a medium. The sample can be in liquid communication with at least one sensor. This communication exposes the at least one sensor to volatile organic compounds produced by the microorganisms. The method can then include predicting an antibiotic resistance profile of the microorganisms to at least one substance based on a response over time of the sensor element to the volatile organic compounds produced by the microorganisms. In some implementations, the liquid communication can further comprise gaseous communication.

Advantages described herein include species identification and susceptibility assay to be complete less than 24 hours after samples reach the laboratory.

BRIEF DESCRIPTION OF DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 5A depicts an example sensor array prior to exposure to an analyte.

FIG. 5B depicts an example sensor array after to exposure to an analyte. FIG. 5C depicts an illustration of a difference map (not based on actual sample).

Figure 1:
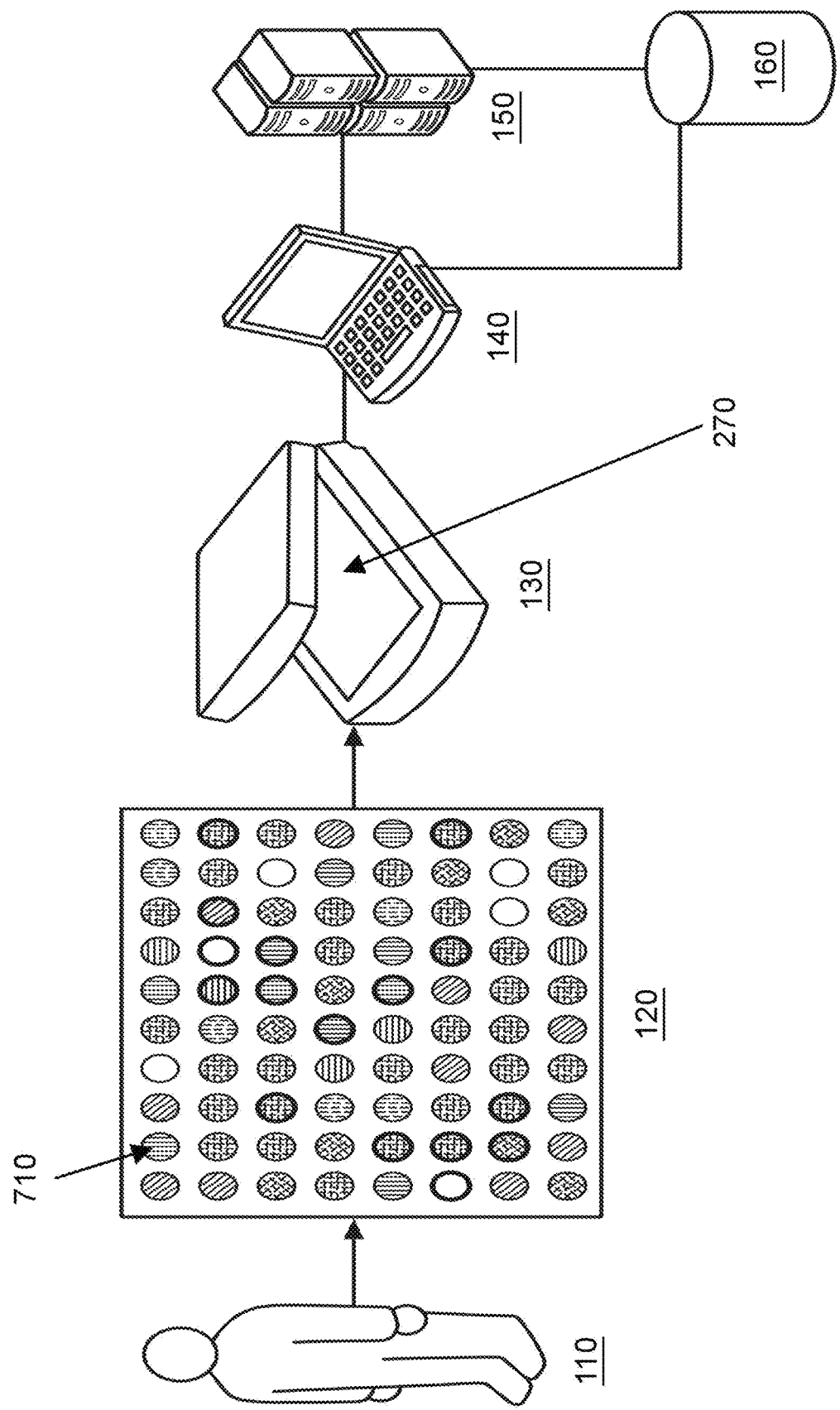
FIG. 1 depicts an example diagram of a system for detecting an array response.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Artificial Nose Technology

VOC selective detectors or "artificial noses" have developed to detect and characterize gaseous samples. A multitude of technologies have implemented artificial nose functions including, but not limited to: colorimetric sensor arrays, polymer arrays, mass sensitive piezoelectric substrates, surface acoustic wave (SAW) transducers, quartz crystal microbalances, functionalized carbon nanotubes and gold nano particles.

Initial work in the field of artificial noses was conducted by Wilkens and Hatman in 1964, though the bulk of research done in this area has been carried out since the early 1980's. See, e.g., W. F. Wilkens, A D. Hatman. Ann. NY Acad. Sci., 116, 608 (1964); K. Pursaud, G. H. Dodd. Nature, 299, 352-355 (1982); and J. W. Gardner, P. N., Bartlett. Sensors and Actuators B, 18-19, 211-220 (1994). Vapor-selective detectors or "artificial noses" are typically based upon the production of an interpretable signal or display upon exposure to a vapor emitting substance or odorant (hereinafter sometimes referred to as an "analyte"). More specifically, typical artificial noses are based upon selective chemical binding or other molecular interactions in the interface between a detecting compound of the artificial nose and an analyte or odorant, and then transforming that chemical binding into a signal or display, i.e., signal transduction.

Polymer arrays having a single dye have been used for artificial noses. That is, a series of chemically-diverse polymers or polymer blends are chosen so that their composite response distinguishes a given odorant or analyte from others. Examples of polymer array vapor detectors, including conductive polymer and conductive polymer/carbon black composites, are discussed in: M. S. Freund, N. S. Lewis, Proc. Natl. Acad. Sci. USA 92, 2652-2656 (1995); B. J. Doleman, R. D. Sanner, E. J. Severin, R. H. Grubbs, N. S. Lewis, Anal. Chem. 70, 2560-2564 (1998); T. A Dickinson, J. White, J. S. Kauer, D. R. Walt, Nature 382, 697-700 (1996)(polymer array with optical detection); A E. Hoyt, A J. Ricco, H. C. Yang, R. M. Crooks, J. Am. Chem. Soc. 117, 8672 (1995); and J. W. Grate, M. H. Abraham, Sensors and Actuators B 3, 85-111 (1991)

Other interface materials include functionalized self-assembled monolayers (SAM), metal oxides, and dendrimers.

Signal transduction is commonly achieved with mass sensitive piezoelectric substrates, surface acoustic wave (SAW) transducers, or conductive materials. Optical transducers (based on absorbance or luminescence) have also been examined. Examples of metal oxide, SAM, and dendrimer-based detectors are discussed in J. W. Gardner, H. V. Shurmer, P. Corcoran, Sensors and Actuators B 4, 117-121 (1991); J. W. Gardner, H. V. Shurmer, T. T. Tan, Sensors and Actuators B 6, 71-75 (1992); and R. M. Crooks, A. J. Ricco, Acc. Chem. Res. 31, 219-227 (1998). These devices also use a single dye.

Techniques have also been developed using a metalloporphyrin for optical detection of a specific, single gas such as oxygen or ammonia, and for vapor detection by chemically interactive layers on quartz crystal microbalances. See A. E. Baron, J. D. S. Danielson, M. Gonterman, J. R. Wan, J. B. Callis, Rev. Sci. Instrum. 64, 3394-3402 (1993); J. Kavandi, et al., Rev. Sci. Instrum. 61, 3340-3347 (1990); W. Lee, et al., J. Mater. Chem. 3, 1031-1035 (1993); A. A. Vaughan, M. G. Baron, R. Narayanaswamy, Anal Comm. 33, 393-396 (1996); J. A J. Brunink, et al., Anal. Chim. Acta 325, 53-64 (1996); C. DiNatale, et al., Sensors and Actuators B 44, 521-526 (1997); and C. DiNatale, et al., Mat. Sci. Eng. C 5, 209-215 (1998).

Other techniques include functionalized carbon nanotubes sometimes integrated into a transistor, see DNA-Decorated Carbon Nanotubes for Chemical Sensing Cristian Staii and Alan T. Johnson, Jr, Nano Letters 2005 and functionalized gold nanoparticles see Broza, Y. Y., & Haick, H. (2013). Nanomaterial-based sensors for detection of disease by volatile organic compounds. Nanomedicine, 8(5), 785-806; Barash, O., Peled, N., Hirsch, F. R., & Haick, H. (2009). Sniffing the Unique "Odor Print" of Non-Small-Cell Lung Cancer with Gold Nanoparticles. Small, 5(22), 2618-2624.

Colorimetric Sensor Arrays

Artificial noses based on colorimetric sensor arrays exist that are capable of detecting VOCs at low concentrations and a high degree of accuracy. Colormetric sensor arrays may detect volatile organic compounds by reacting with the compounds and changing color based on the amount and type compounds exposed to the array. The resulting pattern of color changes comprises a high-dimensional fingerprint which enables the identification of complex mixtures, including disease signatures in exhaled breath and in sealed assays. Various colorimetric sensor arrays are described in the following patent publications to Suslick et al. and all of which are incorporated by reference herein in their entirety: U.S. Pat. No. 6,368,558 to Suslick, U.S. Pat. No. 6,495,102, to Suslick, et al., U.S. Pat. No. 7,261,857, to Suslick et al., and U.S. Patent Publication 2008/0199904.

Chemo-Responsive Dyes

Colorimetric sensor arrays utilizing chemo-responsive (chemically responsive) dyes are capable of detecting individual VOC's and complex VOC mixtures down to low part per billion (ppb) concentrations [10, 11, 25]. "Chemo-responsive dyes" refers to any material that absorbs, reflects, and/or emits light when exposed to electromagnetic radiation, or any other indicator that undergoes a change in spectral properties in response to certain changes in its chemical environment. "Change in spectral properties" generally refers to a change in the frequency and/or intensity of the light the colorant absorbs and/or emits. Chemo-responsive dyes may include dyes and pigments.

For example, the following five classes of chemically-responsive dyes may be utilized: (i) metal-ion-containing dyes that respond to Lewis basicity (i.e., electron pair donation, metal ion ligation), (ii) pH indicators that respond to Brønsted acidity/basicity (i.e., proton acidity and hydrogen bonding), (iii) dyes with large permanent dipoles (e.g., solvatochromic dyes) that respond to local polarity, (iv) metal salts that respond to redox reactions. Utilizing this broad spectrum of highly sensitive chemical interactions allows a colorimetric sensor array to detect and identify very diverse classes of metabolite compounds.

For example, for recognition of analytes with Lewis acid/base capabilities, the use of porphyrins and their metal complexes is desirable. Metalloporphyrins are ideal for the detection of metal-ligating vapors because of their open coordination sites for axial ligation, their large spectroscopic shifts upon ligand binding, their intense coloration, and their ability to provide ligand differentiation based on metal-selective coordination. Furthermore, metalloporphyrins are cross-responsive dyes, showing responses to a large variety of different analytes to different degrees and by different color changes.

A Lewis acid/base dye is defined as a dye which has been identified for its ability to interact with analytes by acceptor-donor sharing of a pair of electrons from the analyte. This results in a change in color and/or intensity of color that indicates the presence of the analyte. Lewis acid/base dyes include metal ion-containing or three-coordinate boron-containing dyes. The change in spectral properties for a Lewis acid-base dye may be related to Lewis acid-base interaction and ligand binding, but also to $\square$-$\square$ complexation, hydrogen bonding, and/or polarity changes.

Exemplary Lewis acids include, but are not limited to, metal ion-containing porphyrins (i.e., metalloporphyrins), salen complexes, chlorins, bispocket porphyrins, and phthalocyanines. Diversity within the metalloporphyrins can be obtained by variation of the parent porphyrin, the porphyrin metal center, or the peripheral porphyrin substituents. The parent porphyrin is also referred to as a free base porphyrin, which has two central nitrogen atoms protonated (i.e., hydrogen cations bonded to two of the central pyrrole nitrogen atoms). In one example, a parent porphyrin is the so-called free base form 5,10,15,20-tetraphenylporphyrin ($H_2TPP$), its dianion is 5,10,15,20-tetraphenyl-porphyrinate (-2) (TPP dianion), its metalated complexes, and its acid forms ($H_3TPP^+$ and $H_4TPP^{+2}$). This porphyrin may form metalated complexes, for example, with $Sn^{4+}$, $Co^{3+}$, $Co^{2+}$, $Cr^+$, $Mn^{3+}$, $Fe^{3+}$, $Cu^{2+}$, $Ru^{2+}$, $Zn^{2+}$, $Ag^{2+}$, $In^{3+}$, and $Ir^{3+}$. Metal ion-containing metalloporphyrin dyes are described, for example, in U.S. Pat. No. 6,368,558 to Suslick et al. and in U.S. Patent Application Publication No. 2003/0143112 to Suslick et al., both of which are incorporated by reference herein. Particularly suitable metal ions complexed with dyes for detecting ammonia include Zn(II) and Co(III) metals. In particular embodiments of the present invention, the Lewis acid dye is a metalloporphyrin. For example, diversity within the metalloporphyrins can be obtained by variation of the parent porphyrin, the porphyrin metal center, or the peripheral porphyrin substituents. The parent porphyrin is also referred to as a free base porphyrin, which has two central nitrogen atoms protonated (i.e., hydrogen cations bonded to two of the central pyrrole nitrogen atoms). A particularly suitable parent porphyrin is 5,10,15,20-tetraphenylporphyrinate(-2) (TPP dianion), its metalated complexes, its so-called free base form (H2TPP) and its acid forms (H3TPP+ and H4TPP+2). Suitable metal ion-containing metalloporphyrin dyes for use in the apparatus and method of the present invention include, but are not limited to:

2,3,7,8,12,13,17,18-octafluoro-5,10,15,20-tetrakis-(pentafluorophenyl)porphyrinatocobalt(II) [Co(F28TPP)];

2,3,7,8,12,13,17,18-octabromo-5,10,15,20-tetraphenylporphyrinatozinc(II) [Zn(Br8TPP)];

5,10,15,20-tetraphenylporphyrinatozinc(II) [ZnTPP];

5(phenyl)-10,15,20-trikis(2',6'-bis(dimethyl-t-butylsiloxyl)phenyl) porphyrinatozinc(II) [Zn(Si6PP)];

5,10,15,20-tetrakis(2',6'-bis(dimethyl-t-butylsiloxyl)phenyl)porphyrinatozinc(II) [Zn (Si8PP];

5,10,15,20-Tetraphenyl-porphyrinatocobalt (II) [CoTPP];

5,10,15,20-Tetrakis(2,6-difluorophenyl)porphyrinatozinc (II) [Zn-F2PP]; and 5,10,15,20-Tetrakis(2,4,6-trimethylphenyl)porphyrinatozinc(II) [ZnTMP].

The synthesis of such porphyrins is is described in U.S. patent application Ser. No. 10/279,788.

pH Sensitive Dyes

The chemoresponsive dye may be, for example, a pH sensitive dye. Dyes that are pH sensitive include pH indicator or acid-base indicator dyes that may change color upon exposure to acids or bases. A Brønsted acid dye of the present disclosure is a pH indicator dye which changes color in response to changes in the proton (Brønsted) acidity or basicity of the environment. For example, Brønsted acid dyes are, in general, non-metalated dyes that are proton donors which can change color by donating a proton to a Brønsted base (i.e., a proton acceptor). Brønsted acid dyes include, but are not limited to, protonated, but non-metalated, porphyrins, chlorins, bispocket porphyrins, phthalocyanines, and related polypyrrolic dyes. Polypyrrolic dyes, when protonated, are, in general, pH-sensitive dyes (i.e., pH indicator or acid-base indicator dyes that change color upon exposure to acids or bases).

In one embodiment, a Brønsted acid dye is a non-metalated porphyrin such as 5,10,15,20-tetrakis(2',6'-bis(dimethyl-t-butylsiloxyl)phenyl)porphyrin dication [H4Si8PP]+2; 5,10,15,20-Tetraphenyl-21H,23H-porphine [H2TPP]; or 5,10,15,20-Tetraphenylporphine dication [H4TPP]+2. In another embodiment of the instant invention, a selected Brønsted dye is an indicator dye including, but not limited to, Bromocresol Purple, Cresol Red, Congo Red, Thymol Blue, Bromocresol Green, Nile Red, Bromothymol Blue, Methyl Red, Nitrazine Yellow, Phenol Red, Bromophenol Red, Disperse Orange 25, and Bromophenol Blue. As will be appreciated by the skilled artisan, the Brønsted acids disclosed herein may also be considered Brønsted bases under particular pH conditions. Likewise, a non-metalated, non-protonated, free base form of a bispocket porphyrin may also be considered a Brønsted base. However, these dye forms are also expressly considered to be within the scope of the dyes disclosed herein.

Examples of Brønsted acid dyes include protonated, but non-metalated, porphyrins; chlorines; bispocket porphyrins; phthalocyanines; and related polypyrrolic dyes. Examples of non-metalated porphyrin Brønsted acid dyes include 5,10,15,20-tetrakis(2',6'-bis(dimethyl-t-butylsiloxyl)phenyl)porphyrin dication; 5,10,15,20-tetraphenyl-21H,23H-porphyrin; or 5,10,15,20-tetraphenylporphyrin dication. Other examples of Brønsted acid dyes include Chlorophenol Red, Bromocresol Green, Bromocresol Purple, Bromothymol Blue, Bromopyrogallol Red, Pyrocatechol Violet, Phenol Red, Thymol Blue, Cresol Red, Alizarin, Mordant Orange, Methyl Orange, Methyl Red, Congo Red, Victoria Blue B, Eosin Blue, Fat Brown B, Benzopurpurin 4B, Phloxine B, Orange G, Metanil Yellow, Naphthol Green B, Methylene Blue, Safranine O, Methylene Violet 3RAX, Sudan Orange G, Morin Hydrate, Neutral Red, Disperse Orange #25, Rosolic Acid, Fat Brown RR, Cyanidin chloride, 3,6-Acridineamine, 6'-Butoxy-2,6-diamino-3,3'-azodipyridine, para-Rosaniline Base, Acridine Orange Base, Crystal Violet, Malachite Green Carbinol Base, Nile Red, Nile Blue, Nitrazine Yellow, Bromophenol Red, Bromophenol Blue, Bromoxylenol Blue, Xylenol Orange Tetrasodium Salt, 1-[4-[[4-(dimethylamino)phenyl]azo]phenyl]-2,2,2-trifluoroethanone-, 4-[2-[4-(dimethylamino)phenyl]ethenyl]-2,6-dimethyl-pyrylium perchlorate, and 1-amino-4-(4-decylphenylazo)-naphthalene.

Solvachromatic Dyes

The chemoresponsive dye may be, for example, a solvatochromic dye or a vapochromic dye. Solvatochromic dyes that may be utilized change color in response to changes in the general polarity of their environment, primarily through strong dipole-dipole and dispersion interactions. To some extent, all dyes inherently are solvatochromic, with some being more responsive than others. Particular examples of suitable solvatochromic dyes include, but are not limited to Reichardt's dyes, 4-hydroxystyryl-pyridinium dye, 4-methoxycarbonyl-1-ethylpyridinium iodide, and 2,6-diphenyl-4-(2,4,6-triphenyl-1-pyridinio)-phenolate.

The addition of at least one Brønsted acid dye to an array containing at least one metal ion-containing Lewis acid dye can improve the sensitivity of the array for particular analytes and increase the ability to discriminate between analytes. For example, colorimetric sensor arrays have been shown to detect volatile organic compounds and complex mixtures down to ppb levels (Rakow, et al. (2005) Angew. Chem. Int. Ed. 44:4528-4532). Further, the use of one or more metal ion-containing dyes in combination with one or more Brønsted acid dyes can advantageously create a signature indicative of the presence of a particular analyte. Thus, while some embodiments may utilize at least one Lewis acid and/or base dye, one Brønsted acidic and/or basic dye, or one zwitterionic solvatochromic dye, other embodiments of this disclosure may utilize at least two different classes of dyes on the instant arrays. In one embodiment, the colorimetric sensor array contains at least one Lewis acid and/or base dye, one Brønsted acidic and/or basic dye, or one zwitterionic solvatochromic dye. In another embodiment, the colorimetric sensor array contains at least one Lewis acid and/or base dye and one Brønsted acidic and/or basic dye. In a further embodiment, the colorimetric sensor array contains at least one Lewis acid and/or base dye and one zwitterionic solvatochromic dye. In yet a further embodiment, the colorimetric sensor array contains at least one Brønsted acidic and/or basic dye and one zwitterionic solvatochromic dye. Still further embodiments may utilize at least three different classes of dyes on the instant arrays, i.e., at least one Lewis acid and/or base dye, one Brønsted acidic and/or basic dye, and one zwitterionic solvatochromic dye.

An array that includes a pH sensitive dye and/or a solvatochromic or vapochromic dye may be useful in differentiating analytes that do not bind to, or bind only weakly to, metal ions. Such analytes include acidic compounds, such as carboxylic acids, and certain organic compounds lacking ligatable functionality. Examples of organic compounds lacking ligatable functionality include simple alkanes, arenes, and some alkenes and alkynes, especially if sterically hindered. Examples of organic compounds lacking ligatable functionality also include molecules that are sufficiently sterically hindered to preclude effective ligation. Arrays that include a pH sensitive and/or a solvatochromic or vapochromic dye are described, for example, in U.S. Patent Application Publication No. 2003/0143112 to Suslick et al., which is incorporated by reference herein.

Redox Sensitive Dyes

The chemoresponsive dye may be, for example, a redox sensitive dye that undergoes a change in spectral properties depending upon its oxidation state. Examples of dyes that are redox sensitive include redox indicators such as methylene blue, naphthol blue-black, brilliant ponceau, .alpha.-naphthoflavone, basic fuchsin, quinoline yellow, thionin acetate, methyl orange, neutral red, diphenylamine, diphenylaminesulfonic acid, 1,10-phenanthroline iron(II), permanganate salts, silver salts, and mercuric salts.

Metal Ion Sensitive Dyes

The chemoresponsive dye may be, for example, a metal ion sensitive dye that undergoes a change in spectral properties in the presence of metal ions. Examples of dyes that are metal ion sensitive include metal ion indicator dyes such as eriochrome black T, murexide, 1-(2-pyridylazo)-2naphthol, and pyrocatechol violet.

Chemoresponsive Pigments

The chemoresponsive dye may be a chemoresponsive pigment. In some cases, the chemoresponsive pigment is a porous pigment. A porous pigment particle has a chemoresponsive surface area that is much greater than the chemoresponsive surface area of a corresponding nonporous pigment particle. Examples of porous pigments include porous calcium carbonate, porous magnesium carbonate, porous silica, porous alumina, porous titania, and zeolites.

Chemoresponsive Nanoparticle

The chemoresponsive colorant may be a chemoresponsive nanoparticle. A chemoresponsive nanoparticle may be a discrete nanoparticle, or it may be formed from nanoparticle-forming ions or molecules. The nanoparticle may be in a variety of forms, including a nanosphere, a nanorod, a nanofiber, and a nanotube. Examples of chemoresponsive nanoparticles include nanoporous porphyrin solids, semiconductor nanoparticles such as quantum dots, and metal nanoparticles.

Array of Dyes

The use of more than one type of chemoresponsive colorant may expand the range of analytes to which the array is sensitive, may improve sensitivity to some analytes, and/or may increase the ability to discriminate between analytes. In some cases, a colorimetric array includes 2 to 1,000 sensors, 4 to 500 sensors, or 8 to 250 sensors. In certain cases, a colorimetric array includes from 10 to 100 sensors (e.g., 16 to 80 sensors, 36 sensors, or 60 sensors). Each sensor in a colorimetric array may include a different colorant. However, it may be desirable to include duplicate sensors that include the same colorant. Duplicate sensors may be useful, for example, to provide redundancy to the array and/or to serve as an indicator for quality control. Table 1 lists exemplary chemoresponsive colorants for a colorimetric sensor array having 36 sensors.

TABLE 1

Exemplary chemoresponsive colorants for a colorimetric sensor array.

| No. | Colorant |
| --- | --- |
| 1 | 5,10,15,20-Tetraphenyl-21H,23H-porphine zinc |
| 2 | 5,10,15,20-Tetraphenyl-21H,23H-porphine copper(II) |
| 3 | 5,10,15,20-Tetraphenyl-21H,23H-porphine manganese(III) chloride |
| 4 | 2,3,7,8,12,13,17,18-Octaethyl-21H,23H-porphine iron(III) chloride |
| 5 | 5,10,15,20-Tetraphenyl-21H,23H-porphine cobalt(II) |
| 6 | meso-Tetra(2,4,6-trimethylphenyl)porphine |
| 7 | Nitrazine Yellow (basic) |
| 8 | Methyl Red (basic) |
| 9 | Chlorophenol Red (basic) |

TABLE 1-continued

Exemplary chemoresponsive colorants for a colorimetric sensor array.

| No. | Colorant |
| --- | --- |
| 10 | Napthyl Blue Black |
| 11 | Bromothymol Blue (basic) |
| 12 | Thymol Blue (basic) |
| 13 | m-Cresol purple (basic) |
| 14 | Zinc (II) Acetate with m-Cresol purple (basic) |
| 15 | Mercury (II) Chloride with Bromophenol Blue (basic) |
| 16 | Mercury (II) Chloride with Bromocresol Green (basic) |
| 17 | Lead (II) Acetate |
| 18 | Tetraiodophenolsulfonephthalein |
| 19 | Fluorescein |
| 20 | Bromocresol Green |
| 21 | Methyl Red |
| 22 | Bromocresol Purple |
| 23 | Bromophenol Red |
| 24 | Brilliant Yellow |
| 25 | Silver nitrate + Bromophenol Blue (basic) |
| 26 | Silver nitrate + Bromocresol Green (basic) |
| 27 | Cresol Red (acidic) |
| 28 | Disperse Orange 25 |
| 29 | m-Cresol Purple |
| 30 | Nitrazine Yellow |
| 31 | Cresol Red |
| 32 | Bromocresol Green |
| 33 | Phenol Red |
| 34 | Thymol Blue |
| 35 | Bromophenol Blue |
| 36 | m-Cresol Purple |

Dye Substrate

In accordance with the present invention, the plurality of chemo-responsive dyes may be deposited on an array substrate in a predetermined pattern combination. Alternatively stated, the dyes are arranged in a two-dimensional (or linear or other arrangement) spatially-resolved configuration so that upon interaction with one or more analytes, a distinct color and intensity response of each dye creates a signature indicative of the one or more analytes. A plurality of chemo-responsive dyes encompasses 2, 3, 4, 5, 6, 7, 8, 9, 10, 15, 20, 25, 30, 35, 40, or 50 individual dyes. In particular embodiments, a plurality of chemo-responsive dyes is 2 or more, 5 or more, 10 or more, 15 or more, 20 or more, 25 or more, or 30 or more dyes. The chemo-responsive dyes can be deposited in predetermined pattern combinations of rows, columns, spirals, etc., and one or more chemo-responsive dye arrays can be used in a container. Dyes can be covalently or non-covalently affixed in or on a colorimetric sensor array substrate by direct deposition, including, but not limited to, airbrushing, ink-jet printing, screen printing, stamping, micropipette spotting, or nanoliter dispensing.

The substrate for retaining the chemo-responsive dyes may be any suitable material or materials, including but not limited to, chromatography plates, paper, filter papers, porous membranes, or properly machined polymers, glasses, or metals. In some embodiments, the substrate may include a hydrophobic substrate. In some embodiments, a nanoporous sol-gel matrix is used as a substrate for the dyes.

A nano-porous pigment may be fabricated by the immobilization of chemically responsive dyes in organically modified siloxanes (ormosils). In some embodiments, the pigment is created by utilizing an electronic spray to generate an aerosol from precursor solutions containing the dye and other materials, which is then heated to form dye encapsulated microspheres. These dye-encapsulated microspheres can then be printed on paper, such as chromatography paper to form a colorimetric sensor array. These porous sol-gel ormosils may provide a good matrix for colorants due to high surface area, good stability over a wide range of pH, relative inertness in many environments, and transparency in the UV-visible spectrum.

A nanoporous sol-gel matrix has enormous surface area at a microscopic scale, which results in the part-per-billion (ppb) sensitivity. In some embodiments, a nanoporous sol-gel matrix may be required to detect the trace volatile organic compound (VOC) signatures of lung cancer and other diseases in urine or other biological fluids. The nanoporous pigment is a silicon-based sol-gel with enormous surface area, vastly increasing interaction opportunities between analyte and indicator and thereby achieving great sensitivity across a wide range of volatile molecules, including species crucial for cancer diagnosis. Furthermore, the high chemical resistance of the nanoporous pigment allows a manufacturer to increase the chemical diversity of the dyes deposited on the nanoporous substrate that were by adding chromogenic reagents that were too reactive to incorporate onto substrates comprised of different materials. Nanoporous pigments are more fully described in Lim et al., Chemically Responsive Nanoporous Pigments: Colorimetric Sensor Arras and the Identification of Aliphatic Amines, Langmuir 24 (22), 2008, which is incorporated by reference herein in its entirety.

Exposure of the Array to Analytes

For gas or vapor analytes, a gas stream containing the analyte is passed over the array, and images may be obtained before, during and/or after exposure to the gas stream. Preferably, an image is obtained after the sample and the array have equilibrated. If the gas stream is not pressurized, it may be useful to use a miniaturized pump.

For analytes dissolved in a solvent, either aqueous or non-aqueous, the first image may be obtained in air or, preferably, after exposure to the pure carrier solvent that is used of the sample. The second image of the array may be obtained after the start of the exposure of the array to the sample. Preferably an image is obtained after the sample and the array have equilibrated.

A colorimetric array may be used to detect analytes in exhaled breath. Detection of compounds in exhaled breath can be useful in detecting infection or disease. The colorimetric detection of ammonia in exhaled breath is described, for example, in U.S. Patent Application Publication No. 2005/0171449 to Suslick et al., which is incorporated by reference herein.

The colorimetric sensor array may be in gaseous communication with a fluid sample and/or a solid or liquid culture medium, or other materials containing the sample. This will allow volatile organic compounds emitted from the sample (e.g. from microorganisms in the sample) to evaporate into the air in the container and come into contact with the colorimetric sensor array. In some embodiments, the container is sealed, and colorimetric sensor array is exposed to volatile organic compounds emitted from the microorganisms or other sources of VOCs. In other embodiments, different containers or other mechanisms could be utilized to expose the colorimetric sensor array to gas emitted from the sample. This could include various channels or tubing that could transport the volatile organic compounds emitted from the sample into a gaseous state.

Detection of Artificial Nose Response

Detector

In embodiments where a colorimetric sensor array is utilized as the artificial nose technology, the color changes of the chemically responsive dyes may be detected by any suitable optical or other detector. In embodiments pertaining to a colorimetric sensor array, a detector may monitor the spectroscopic response, transmission response or reflectance response of the dyes on the colorimetric sensing element at one or more wavelengths in a spatially resolved fashion so that all of the spots in the colorimetric sensor array are individually imaged or addressed and the color of each spot is individually determined. For the purposes of the present disclosure, the terms color and colorimetric are intended to include wavelengths in the visible portion of the electromagnetic spectrum, as well as the invisible portion of the electromagnetic spectrum, e.g., infrared and ultraviolet.

Color detection can be accomplished with an imaging spectrophotometer, a flatbed scanner, slide scanner, a video or CCD or CMOS digital camera, or a light source combined with a CCD or CMOS detector. Any still or video as well as analog or digital camera can be employed. Moreover, any imaging format can be used, e.g., RGB (red, green and blue) or YUV. Even the simple grayscale imaging can be used. In other embodiments utilizing other artificial nose technologies, a detector or sensor may similarly be used to provide a response of the detector indicative of the molecular interactions occurring at the detector probe or other sensor.

The sensitivity of a colorimetric sensor array is primarily a function of two factors, the ability of a dye spot to change color when exposed to an analyte and the ability of the detector to detect that color change.

In some embodiments, an optical spectroscopic measurement system can divide the visible spectrum into many individual bandpass windows whereas a three-color imaging system by definition contains only three such windows. An optical spectroscopic measurement system is therefore capable of detecting smaller color changes than can be detected by three-color imaging systems, effectively increasing the sensitivity of the entire cross-responsive sensing system. Accordingly, in particular embodiments of the present disclosure, an optical spectroscopic measurement system is employed as a detector. As used herein, optical spectroscopic measurement systems refer to any system that yields higher color resolution than a three-color imaging system. This can be an imaging spectrograph, fiber optic probe(s) coupled to a spectrograph, or other spectroscopic system.

Detection Process and System Setup

Figure 2:
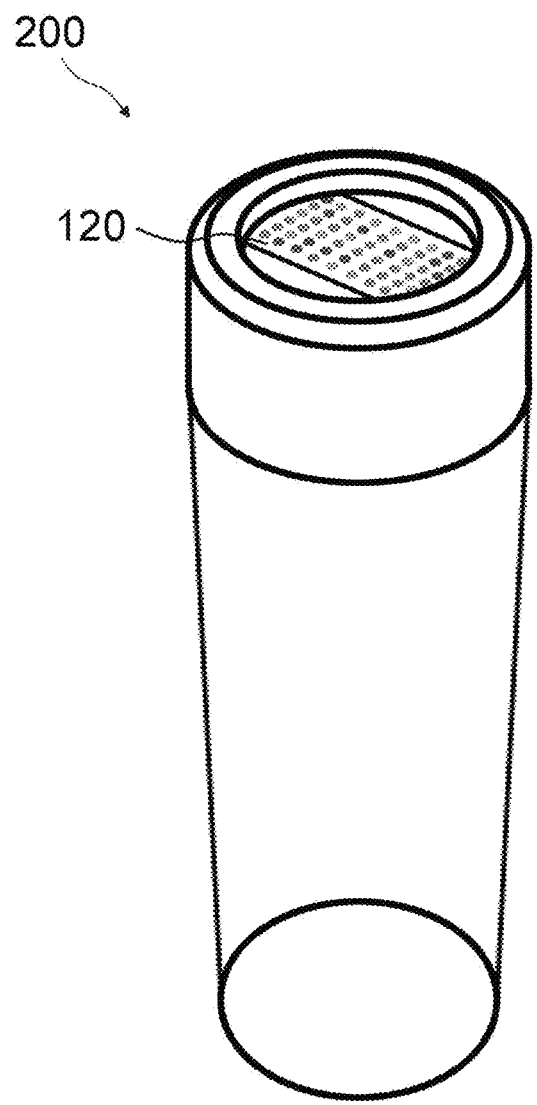
FIG. 2 depicts a perspective view of an example container and sensor array.

FIG. 1 illustrates an example of a system, in some embodiments, the sample and container 200 (as shown in FIG. 2) are maintained at a constant temperature by an incubator. Referring back to FIG. 1, in some embodiments, the detector 130 may be incorporated into an incubator to allow the detector to continuously, or intermittently record the colorimetric response of the dyes 710 through window 270 while leaving the containers 200 undisturbed at constant temperature. After application of the VOCs contained in the urine may begin to react with the colorimetric sensor array 120.

Prior to application of a sample, a detector 130 may record an image of the presently loaded sensor array 120 as a control for later comparison and subtraction of color changes. Accordingly, this will allow the system to measure color changes based on variation from that particular array's initial color profile. In embodiments associated with other artificial nose technologies, the detector may record an initial reading for comparison to a later reading after introduction of a sample. After application of a sample to a sensor container 200, a detector 130 may at various intervals or after a set time interval, detect and record the colorimetric response of the dyes 710 or other detector 130 response. In some embodiments, software may be configured on server 150 or processing device 140 for automatically controlling the precise timing of detector 130 and recording of the data captured by detector 130. For example, the detector 810 may record an image every minute, every 2, 3, 4, 5, 6, 7, 8, 9 or 10 minutes, or at intervals in-between, or at 20 or 30 minutes, or other suitable intervals. In some embodiments, the detector 130 may continuously record data from the colorimetric sensor array 120. The detector 130 may record images for an hour, 2, 3, 4, 5, or 6 hours, or other suitable time frame. In some embodiments, the time frame may be selected based on when the color change rate is near homeostasis or has stopped reacting. In other embodiments, the color change may be stopped when a color change rate drops below a certain threshold.

FIG. 2 depicts exemplary container 200 with colorimetric sensor array 120 for detecting volatile organic compounds emitted from a sample. Container 200 may include a solid or liquid culture medium generally known in the art. A sample, such as a fluid sample (e.g., blood, sputum, exhaled breath) from a mammal, a tissue sample from a mammal, or the like, is placed or injected in container 200.

Figure 3:
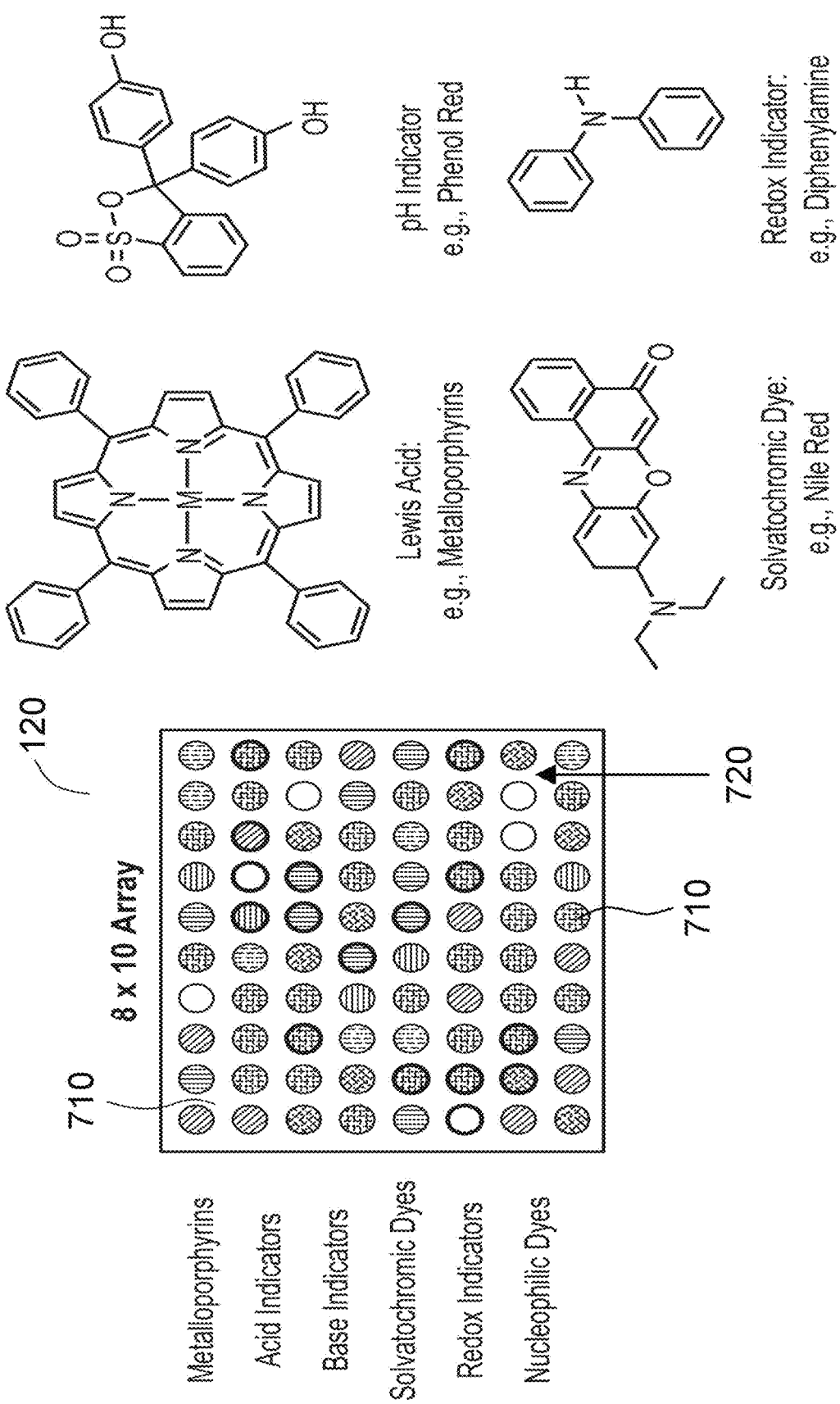
FIG. 3 depicts a diagram of an example sensor array.

FIG. 3 illustrates an embodiment of a colorimetric sensor array 120. In an embodiment, a colorimetric sensor array 120 may include a substrate 720 upon which a variety of chemically responsive dyes 710 may be deposited. The dyes 710 may change color after exposure to and reacting with volatile organic compounds. Certain dyes are responsive to certain VOCs allowing for a particular mixture of VOCs to be determined by its unique color change exhibited on the sensor array 120.

Data Processing

Data output from the detector 130 or other instruments associated with an artificial nose technology may then be stored and later processed for evaluation and diagnosis of the sample. A detector 130 may be incorporated into any suitable sensor or other instruments associated with an artificial nose technology system. The processing of the data may be performed on the processing device 140, server 150, or other computing device connected to the system. Various artificial nose technologies and systems may provide a response or an output indicative of the chemical or molecular interactions occurring at a sensor associated with the artificial nose technology. For example, many embodiments may utilize a detector 130 to detect changes after introduction of a urine sample containing VOCs.

Processing Detector Data for Colorimetric Sensor Array

In embodiments utilizing a colorimetric sensor array based artificial nose, a detector 130 may be utilized to detect optical changes in the array 120. In some embodiments, the detector 130 may only capture an image of the sensor array 120 before and at a single point in time after exposure of the dye 710 to the sample. In other embodiments, the detector 130 may capture images at various times or continuously after exposure of the sample to the dye 710. The color change differences before and at various points after introduction of the sample are used to classify or determine the properties of the sample. For example, when used in combination with colorimetric sensor array 120 and image analysis software, colorimetric differences can be generated by subtracting the values of dye images generated before and after exposure of the dye to a sample. In some embodiments, the colorimetric differences represent hue and intensity profiles for the array 120 in response to analytes contained in the sample. Thus for each image, the detector 130 may extract a 240-dimensional 16-bit vector (R, G and B values if, for example, 80 indicators are used) before and after exposure. When used in accordance with the method of the present disclosure, a unique color change signature for the sample can be created which provides both qualitative recognition and quantitative analysis of volatile organic compounds present in the sample.

Figure 4:
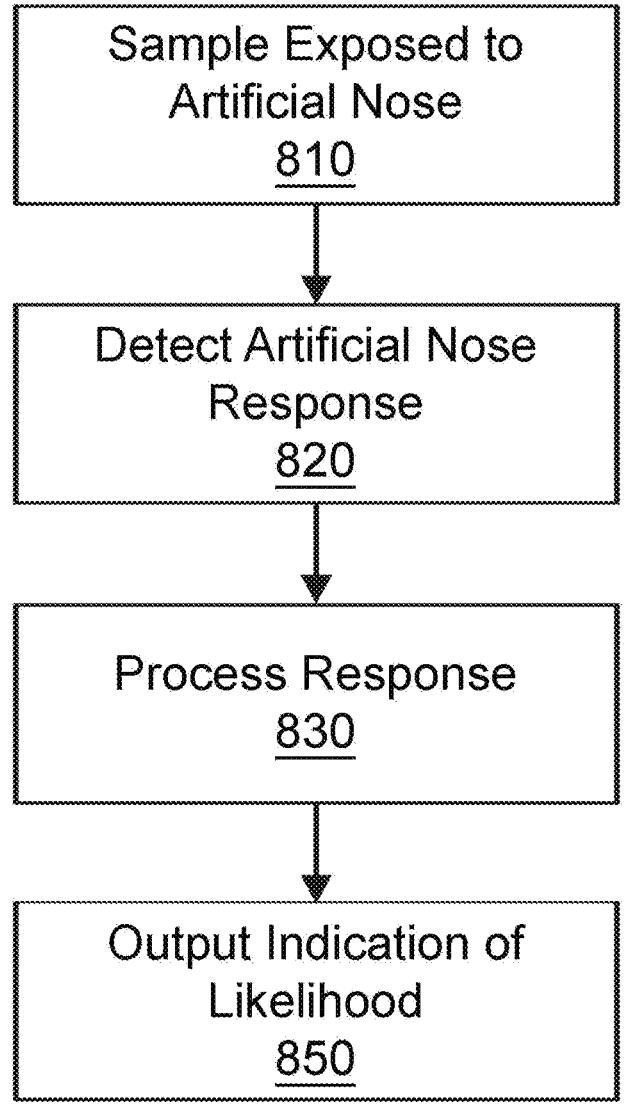
FIG. 4 depicts an example of a method determining a likelihood a patient has a malady based on detecting and processing a sensor response.

FIG. 4 illustrates an example of a process according to an exemplary embodiment of the present disclosure. Certain or all of the steps listed in FIG. 4 may be implemented or controlled by a processing device 140, detector 130, associated database 160, server 150, and other electronic components that are communicating over a network. These computer or processor integrated components can automatically implement the illustrated process to provide an indication of whether a patient has lung cancer.

For example, first a sample may be exposed to an artificial nose 810. This may be implemented by a caregiver applying a sample inside a container 200 or a processing device 140 to open a door or other feature to allow exposure of the sample to the artificial nose 810 to begin. Exposure to the sample could be performed by any suitable method that allows the headspace gas to be exposed to, come in contact with, or come within gaseous proximity to the colorimetric array 120. Next, a response or image or several responses or images as described herein of the colorimetric array or other artificial nose 820 may be captured by a detector 130. In some embodiments, the detector 130 will first capture an image or several images of the colorimetric array or artificial nose 820 as a baseline prior to exposure of the colorimetric array 120 to the sample as described herein. Particularly, responses or readings from technologies may be taken before and after introduction of the sample to the artificial nose sensor or detector 130.

Next, the system may process the image data or other artificial nose response data 830 captured by the detector 130. The processing 830 may be performed by any processing device 140 connected to the system. For example, the system may determine a colorimetric difference between the baseline image and images captured after exposure of the colorimetric sensor array 120 to the headspace gas from the sample.

Then, the system may calculate or determine a likelihood 840 a patient from which the sample came has a malady such as cancer, an infection from a microorganism, and certain information about the disease or microorganisms including its susceptibility to antibiotics. based on the processing of the image or other detector 130 data 830. This may be performed by comparing the colorimetric difference determined in the processing 830 step to a database 160 to colorimetric differences associated with samples belong to patients with known ailments such as infections from microorganisms, cancer, or other maladies. For example, a statistical analysis may be performed using an HCA or PCA analysis (as described more fully herein) to determine the likelihood a sample indicates the associated patient has cancer, an infection, or a drug resistant infection, based on comparisons to differences in the samples in the database that are known to have cancer or lung cancer or based on other processing techniques that filter and identify certain features of the response.

Computer Implementation of Analysis

In order to implement the image-based processing and analysis system, the system may also include a memory storage device operatively coupled to the processor that stores a multiplicity of temporal and/or static color response patterns of known species and/or strains of microorganisms (e.g., bacteria, yeast, protozoa). Thus, the system is operable to generate a temporal and/or static color response pattern of a sample including a microorganism, and automatically identify the microorganism (e.g., by species and strain) by comparing the generated color response pattern of the array 120 with the stored multiplicity of temporal and/or static color response patterns (e.g., the "library") of known species and/or strains of microorganisms. Comparing the generated color response pattern with the library of known species and/or strains of microorganisms may be achieved by one of a number of statistical methods described herein or incorporated by reference.

In other embodiments, information output by detector 130 may be sent to a remote database to be processed and compared to a centralized database to determine the closest matching dataset. In other embodiments, certain portions of the calculation may be performed locally at a processor on the system and some portions may be performed remotely by a processor or other computing device on a server. In some embodiments, a library of datasets with previous data points for known antibiotic strains and/or known resistances or susceptibilities may be contained in the system or in a centralized server. In the server embodiments, the data could be continually updated and stored as more assays are performed and organisms identified along with susceptibilities.

The system may then output an indication of the likelihood 850 to a display associated with the system. The output of the indication may be percentage likelihood a patient has cancer, an infection, a threshold determination of whether the patient should have follow-up screening or testing for cancer or infection, or further testing to validate the results or other suitable indications. The systems and methods disclosed herein may also be able to provide additional quantitative information regarding the diagnosis that may assist a patient in decision making.

Analyzing Images of Arrays

Analyzing the differences between the first image and the second image may include quantitative comparison of the digital images before and after exposure to the analyte. Using customized software or standard graphics software such as Adobe® PhotoShop®, a difference map can be obtained by subtracting the first image from the second image. To avoid subtraction artifacts at the periphery of the spots, the center of each spot can be averaged.

Figure 5A:
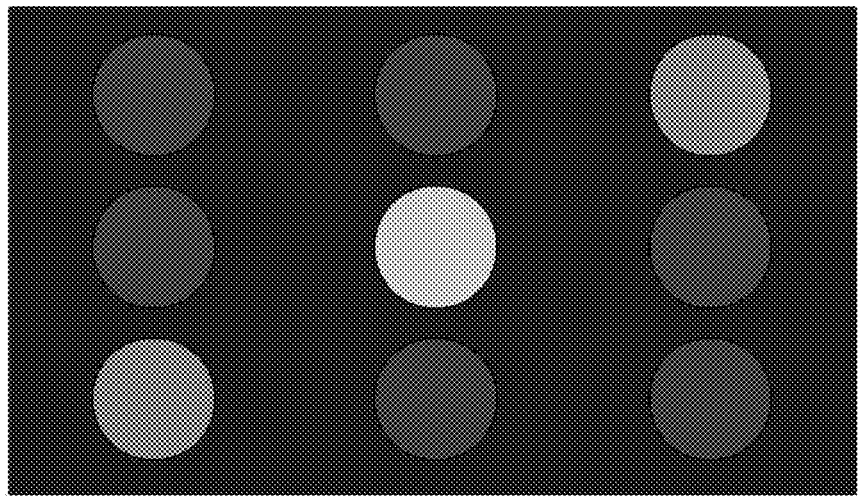
FIGS. 5A-5C depict illustrations of diagrams of an example sensor array after exposure to analytes.
Figure 5B:
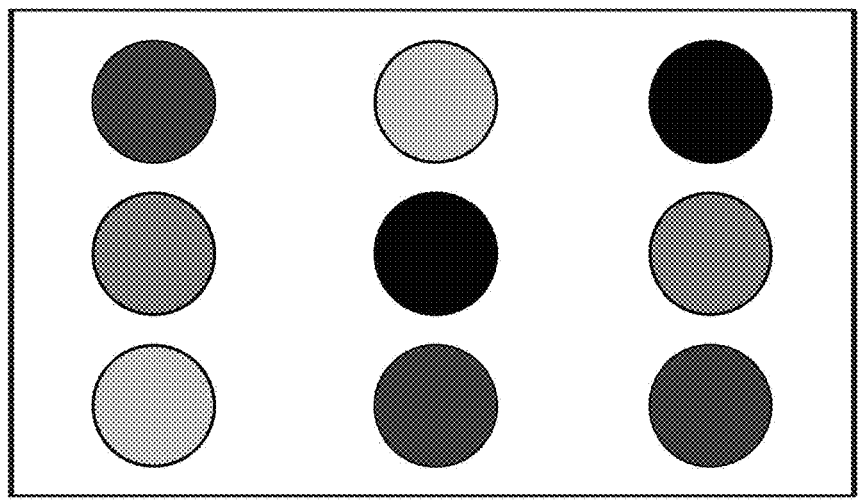
Figure 5C:
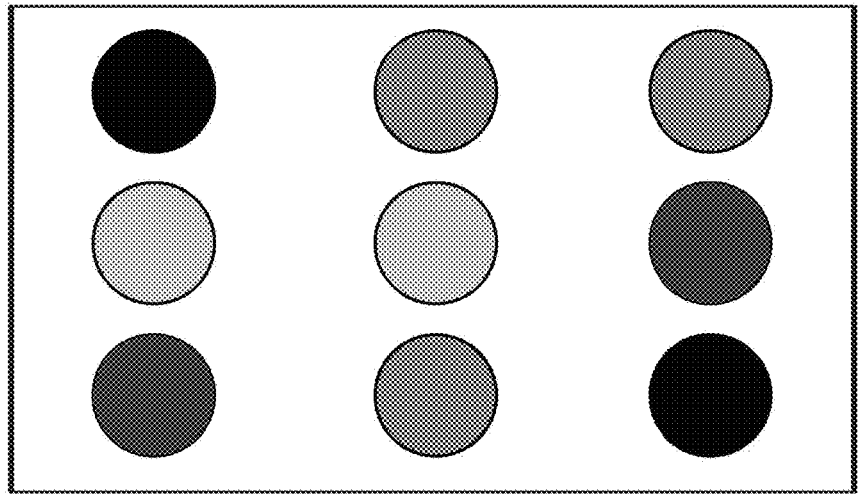

FIGS. 5A-5C are illustrations of an example image from a colorimetric sensor array, showing the array before exposure to *E. coli* 25922 (FIG. 5A), after exposure to *E. coli* 25922 (FIG. 5B), and a difference map of these two images (FIG. 5C). The comparison data obtained from the difference map includes changes in red, green and blue values (ARGB) for each spot in the array. The changes in spectral properties that occur upon exposure to an analyte, and the resultant color difference map, can serve as a unique fingerprint for any analyte or mixture of analytes at a given concentration.

In the simplest case, an analyte can be represented by a single $3x$ vector representing the ARGB values for each colorant, where x is the number of colorants as set forth in equation (1). This assumes that equilibration is relatively rapid and that any irreversible reactions between analyte and colorant are slow relative to the initial equilibration time:

$$\text{Difference vector}=\Delta R1, \Delta G1, \Delta B1, \Delta R2, \Delta G2, \Delta B2, \ldots \\ \Delta Rx, \Delta Gx, \Delta Bx \quad (1)$$

Alternatively, the temporal response of the analyte can be used to make rapid identification, preferably using a "time-stack vector" of ARGB values as a function of time. In equation 2, a time-stack vector is shown for an array of 36 colorants at times m, n, and finally z, all using the initial scan as the baseline for the differences in red, green and blue values:

$$\text{Time stack vector}=\Delta R1m, \Delta G1m, \Delta B1m, \Delta R2m, \Delta G2m, \\ \Delta B2m, -\Delta R36m, \Delta G36m, \Delta B36m, \ldots \Delta R1n, \\ \Delta G1n, \Delta B1n, \ldots \Delta R36m, \Delta G36m, \Delta B36m, \ldots \\ \Delta R36z, \Delta G36z, \Delta B36z \quad (2)$$

Accordingly, each analyte response can be represented digitally as a vector of dimension $3xz$, where x is the number of colorants and z is the number of scans at different times. Quantitative comparison of such difference vectors can be made simply by measuring the Euclidean distance in the $3xz$ space. Such vectors may then be treated by using chemometric or statistical analyses, including principal component analysis (PCA), hierarchical cluster analysis (HCA) and linear discriminant analysis. Statistical methods suitable for high dimensionality data are preferred. As an example, HCA systematically examines the distance between the vectors that represent each colorant, forming clusters on the basis of the multivariate distances between the analyte responses in the multidimensional ΔRGB color space using the minimum variance ("Ward's") method for classification. A dendrogram can then be generated that shows the clustering of the data from the Euclidean distances between and among the analyte vectors, much like an ancestral tree.

CSAs for Identification of Microorganisms

Colorimetric sensor arrays described herein can be used to identify and/or monitor pathogenic and non-pathogenic microorganisms. In one example, a sample including microorganisms from a mammal (e.g., a human) showing symptoms of a malady or showing need of treatment for a malady can be taken from the mammal (e.g., in the form of a fluid sample such as blood or exhaled breath, or in the form of a tissue sample) and cultured in the presence of a colorimetric sensor array. In other examples, microorganisms such as *Saccharomyces cerevisiae* and others can be monitored in processes such as baking and alcoholic fermentation processes, electricity generation in microbial fuel cells, and biofuel production.

Response of the sensors in the colorimetric sensor array to the volatile organic compounds yields a strain-specific temporal or static color response pattern, allowing the microorganism to be identified by comparison of the color response pattern with color response patterns for known strains. Comparison may be achieved, for example, visually or automatically.

While bacteria of a given species share certain characteristics, different strains of the same species yield noticeably different color response patterns (or "fingerprints"), allowing discrimination between strains of the given species (e.g., between *Staphylococcus aureus* and methicillin-resistant *Staphylococcus aureus* and between *Enterococus faecalis* and vancomycin-resistant *Enterococus faecalis*). The color response patterns allow identification of microorganisms by species and strain and certain antibiotic resistant characteristics in a fraction of the time (e.g., about three-quarters of the time, about one-half of the time, or about one-quarter of the time) of other methods, based at least in part on conditions such as concentration, culture medium, culture conditions (e.g., temperature), and the like.

Figure 6:
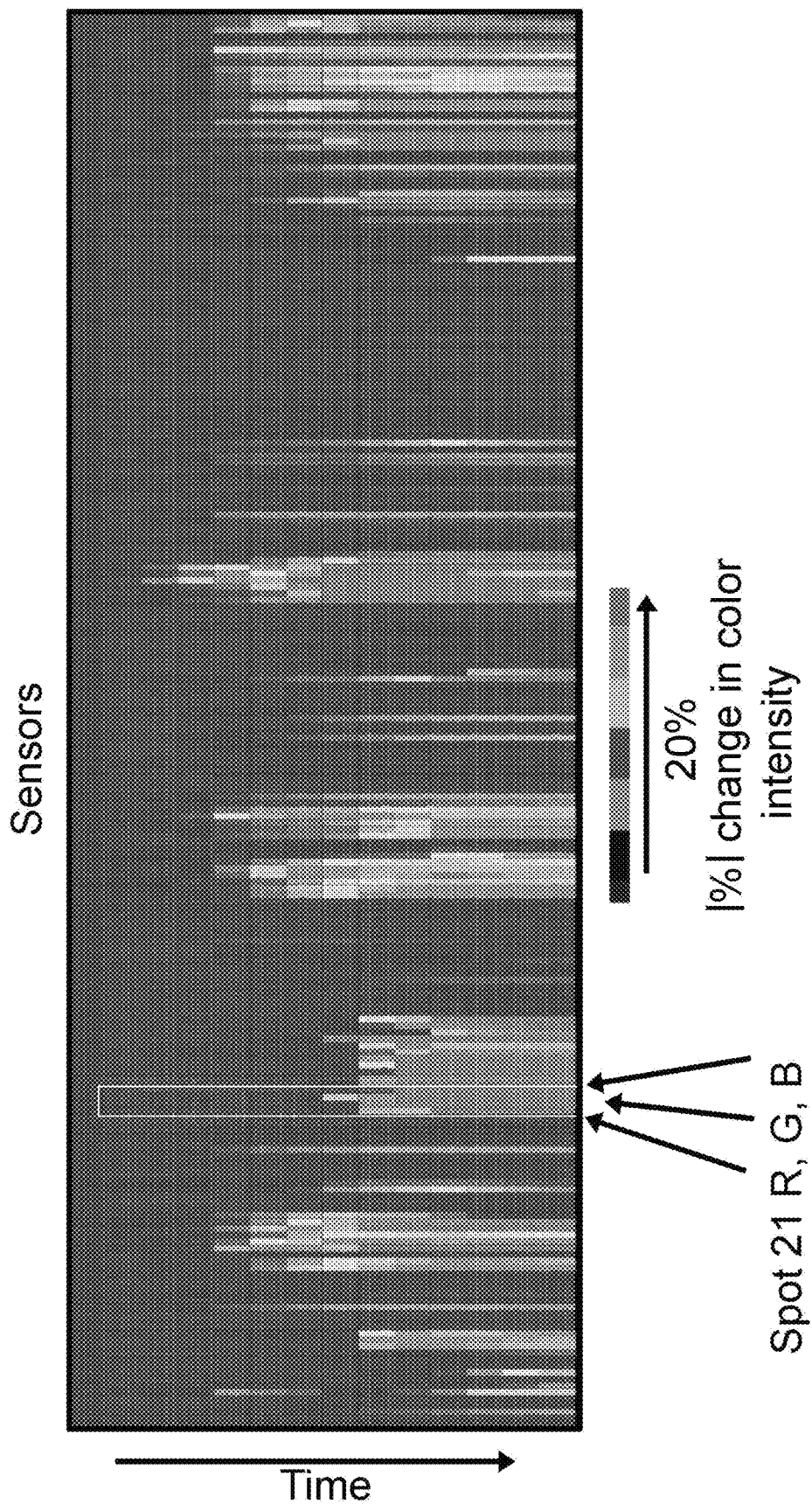
FIG. 6 depicts a heat map of a temporal sensor response.

Microorganisms such as bacteria, yeasts, protozoa, and fungi can be identified as described herein. Species of bacteria that can be identified include, for example, *Staphylococcus aureus, Staphylococcus epidermidis, Staphylococcus sciuri, Pseudomonas aeruginosa, Enterococcus faecium, Enterococcus faecalis, Escherichia coli, Klebsiella pneumoniae, Streptococcus pneumoniae, Streptococcus pyrogenes, Vibrio cholera, Achromobacter xylosoxidans, Burkholderia cepacia, Citrobacter diversus, Citrobacter freundii, Micrococcus leuteus, Proteus mirabilis, Proteus vulgaris, Staphy-* lococcus lugdunegis, Salmonella typhi, Streptococcus Group A, Streptococcus Group B, S. marcescens, Enterobacter cloacae, Bacillis anthracis, Bordetella pertussis, Clostridium sp., Clostridium botulinum, Clostridium tetani, Corynebacterium diphtheria, Moraxalla (Brauhamella) catarrhalis, Shigella spp., Haemophilus influenza, Stenotrophomonas maltophili, Pseudomonas perolens, Pseuomonas fragi, Bacteroides fragilis, Fusobacterium sp. Veillonella sp., Yersinia pestis, and Yersinia pseudotuberculosis. Strains of bacteria that can be identified include, for example, S. aureus 25923, S. aureus 29213, S. aureus 43300, S. aureus IS-13, S. aureus IS-38, S. aureus IS-43, S. aureus IS-70, S. aureus IS-120, S. aureus IS-123, S. aureus IS-124, methicillin-resistant S. aureus 33591, S. epidermidis 35984, S. sciuri 49575, P. aeruginosa 10145, P. aeruginosa IS-15, P. aeruginosa IS-65, P. aeruginosa IS-22, P. aeruginosa IS-36, P. aeruginosa 27853, E. faecium 19434, E. faecalis 23241, vancoymcin-resistant E. faecalis 51299, E. coli 25922, E. coli 53502, E. coli 35218, E. coli 760728, E. coli IS-39, E. coli IS-44, A. xylosoxidans IS-30, A. xylosoxidans IS-35, A. xylosoxidans IS-46, A. xylosoxidans IS-55, C. diversus IS-01, C. diversus IS-28, C. diversus IS-31, C. diversus IS-33, K. pneumoniae IS-130, K. pneumoniae IS-133, K. pneumoniae IS-136, K pneumoniae 33495, B. anthrax Ames, B. anthrax UM23CL2, B. anthrax Vollum, Y. pestis CO92, Y. pestis Java 9, S. epidermis* 12228, *S. epidermis* IS-60, *S. epidermis* IS-61, *P. miribilis* IS-18, *P. miribilis* IS-19, *P. miribilis* 12453, *S. marcescens* IS-48, *S. marcescens* IS-05, and *S. marcescens* 13880, where "IS-#" refers to clinical isolates and the other strains are ATCC® reference strains. Species of fungi that can be identified include, for example, *Microsporum* sp. *Trichophyton* sp. *Epidermophyton* sp., *Sporothrix schenckii, Wangiella dermatitidis, Pseudallescheria boydii, Madurella grisea, Histoplasma capsulatum, Blastomyces dermatitidis, Coccidioides immitis, Cryptococcus neoformans, Aspergillus fumigatus, Aspergillus niger*, and *Candida albicans*. Similarly, yeasts including Ascomycota (*Saccharomycotina, Taphyrinomycotina, Schizosaccharomycetes*) and Basidiomycota (*Agaricomycotina, Tremellomycetes, Pucciniomycotina, Microbotryomycetes*) can be identified and, if desired, assessed for susceptibility. Examples include *Saccharomyces cerevisiae* and *Candida albicans*. Protozoa including *flagellates* (e.g., *Giardia lamblia*), amoeboids (e.g., *Entamoeba histolytica*), sporozoans (e.g., *Plasmodium knowlesi*), and ciliates (e.g., *Balantidium coli*) may also be identified as described herein.

Drug Resistance Signature—Cultured without Antibiotics

It has been discovered the sensor 120 response of a sample cultured without antibiotics (e.g. only in growth medium) additionally provides information regarding the drug resistance of microorganisms in the sample. For instance, in some cases the sensor 120 response or the temporal sensor 120 response may provide additional information about drug resistant profiles of an organism.

This temporal response of one or two indicators or dyes 710 in some cases may provide information regarding the drug resistance of microorganisms in the sample. In some cases, a certain class of dyes 710 that are responsive to a certain class of compounds may provide information or an indication of a drug resistant profile. This may be because the drug resistant microorganisms emit a certain class of compounds, potentially at certain times in their growth cycle that are different from non-drug resistant microorganism.

In other examples, the signature of the response or certain portions of multiple indicators or dyes 710 may indicate the sample contains a drug resistant microorganism. In some examples, the temporal response of certain dyes 710 may indicate a drug resistant microorganism is present. For instance, a certain indicator may be present or increase or decrease a change in spectral properties at an earlier or later time at the start of incubation of the sample in growth media. In some examples, the indicator may change a certain amount by a certain time if the microorganisms have certain types of drug resistance.

The response of the indicators or dyes 710 may indicate different types of drug resistance, including resistance to primary, secondary or tertiary antibiotics. In some examples, the response of the indicators or dyes 710 may indicate a multi-drug resistance profile. This response may be detected prior to the identification of the microorganisms in some cases. In some cases, the response pattern detected for multi-drug resistance may be the same for different species and types of organisms cultured in a sample.

The response of the indicators or dyes 710 on the array 120 may also indicate a mode of resistance exhibited by the microorganism(s) cultured in the sample. For example, there are several known modes through which microorganisms may be resistant to antibiotics. These include (1) developing enzymes that deactivate the antibiotics, (2) alteration of the binding site of the antibiotic, (3) alteration of a metabolic pathway with which the antibiotic interferes, (4) development of cell envelope layers that are impermeable to the antibiotic (or several), and (5) pumps (e.g., efflux) that pump out harmful substances in the microorganism which may confer multi-drug resistance. The response signature of the colorimetric sensor array 120 accordingly may also indicate the modes of resistance of the microorganism to various antibiotics, without culturing the sample or micro-organisms in the presence of antibiotics.

Processing Techniques for Determining Drug Resistance

Various techniques may be utilized as disclosed herein to detect the response patterns of the array 120 and process the patterns to predict or identify samples that contain microorganisms with antibiotic resistance. For instance, as disclosed, the detectors 130 may detect the response patterns at various time points, and compare the patterns to time equals zero, or other times to indicate changes in response from the baseline or changing responses at certain time points.

For instance, the percentage change for each dye 710 or indicator over time may be processed to identify various thresholds or signatures that indicate the micro-organisms cultured may have antibiotic resistance. For instance, system may determine a percentage change in the spectral properties of each of R, G, and B spectrum response of the dyes 710 on the array 120. Accordingly, the response will generally detect changes that indicate changing amounts of analytes at various time periods during the incubation. The percentage changes may include percentage increases or decreases in the spectral intensity of a red, green, or blue spectrum. In other examples, different wavelengths may be detected, or only one wavelength may be analyzed for a threshold change.

In some examples, the system may detect certain patterns of spectral changes over time from a dye or set of dyes 710. This may be spectral changes of intensity that follow a certain rate increase or decrease, follow a pattern of increasing and decreasing, or increase a certain amount or decrease a certain amount in a time window. In some examples, a pattern of increases, decreases, or steady amounts may be identified as relevant to a drug resistance of the microorganisms in a sample.

Accordingly, in some examples, the spectral intensity changes may be plotted on a heat map that shows percentage change of spectral intensity for each of R, G, and B for each dye 710, every 20 minutes for 48 hours. An example of a heat map is illustrated in FIG. 6. These heat maps may be utilized as a first step to reduce the dimensionality of the data, and then may be processed further to identify matching patterns in the data, by correlation methods and others as disclosed herein. The changes in the response may be output or displayed as a heat map that show the changes in response for each dye 710 at increasing intervals of time from the baseline. The changes in response may be displayed as various changes in the spectral properties of the dyes 710.

Accordingly, these signatures of drug resistance may be identified from the image data from various available processing methods. For instance, data sets, or a library of responses from drug resistant organisms may be obtained, and saved in database and analyzed to determine patterns or specific indicators or dyes 710 that have responses indicative of drug resistance. For instance, if it is determined that a subset of the indicators have a relevant response that is predictive of drug resistance, then several measures can be used to identify those changes, including: an average response, a spectral change threshold, a threshold change time window, or other filters.

In some examples, an average sensor response of a set of drug resistant microorganisms may be taken over certain periods of time during incubation. Those average responses could be then filtered to find threshold changes that are significantly present in most or all of the samples. Then correlation and matching algorithms could be utilized to identify those features in new samples, for instance. to find a threshold spectral change or changes in the indicators that turned out to be significant in the averages.

Confirmation with Genomic Assays

Once a drug resistant organism is identified using the disclosed systems and methods, caregivers may use other assays that confirm the results (e.g. GeneXpert assays). Accordingly, the system can begin or modify treatment once a drug resistant infection is identified, then another assay can confirm or further specify the organism and treatment plan.

EXAMPLES

The following examples are provided to better illustrate the claimed invention and are not intended to be interpreted as limiting the scope of the invention. To the extent that specific materials or steps are mentioned, it is merely for purposes of illustration and is not intended to limit the invention. One skilled in the art may develop equivalent means or reactants without the exercise of inventive capacity and without departing from the scope of the invention.

Example 1: Carbapenem Resistant *E. Coli* Signatures

Carbapenem-resistant enterobacteriaceae (CRE) or carbapenemase-producing enterobacteriaceae (CPE) are gram-negative bacteria that are resistant to the carbapenem class of antibiotics, considered the drugs of last resort for such infections. Carbapenems are the most effective antimicrobial agents against gram-positive and gram-negative bacteria. Carbapenems bear a penemic together with the beta-lactam ring and, like all other beta-lactams, they inhibit bacterial cell wall synthesis by binding to and inactivating Penicillin Binding Proteins (PBPs). This unique molecular structure gives them their exceptional stability to many beta-lactamases including AmpC and most of the extended spectrum beta-lactamases (ESBLs). Carbapenem resistance mechanisms have emerged under the pressure of carbapenem use in clinical settings and may be classified as enzymatic, mediated by carbapenemases (beta-lactamases hydrolyzing carbapenems among other beta-lactams), and non-enzymatic, including hyper expression of efflux pumps by mutations. Carbapenem resistance however, develops frequently due to the concomitant presence of more than one mechanism. Additionally, diminished outer membrane permeability prevents antibiotics from entering the cell membrane and provides resistance to certain types of carbapenem.

Carbapenem resistance is a significant cause of morbidity and mortality in hospitals. Strains harboring carbapenem resistance mechanisms compromise severely the selection of appropriate treatments because of the fact that carbapenem resistance is commonly associated with resistance to other antibiotic classes. Consequently, the detection of carbapenem-resistant strains and the implementation of strict infection control measures become critical for limiting the spread of the underlying resistance mechanisms. Accordingly, the ability to detect carbapenem resistance fast is critical in stopping the spread and death of patients with an infection.

Currently, carbapenem resistance currently takes days to identify using laboratory workflows, and therefore frequently can cause death and spread quite fast in hospital settings. For instance, susceptibility testing to determine whether the microorganisms grow in the presence of antibiotics, or tests for carbapenemase enzymes may be performed. Accordingly, it is becoming an increasingly critical problem to address that does not have a fast enough solution.

Accordingly, CRE were cultured in the presence of a sensor 120 to determine whether any unique signatures or patterns could identify carbapenem resistance—in a culture that did not include carbapenem class antibiotics. Surprisingly, a carbapenem drug resistant signature has been identified in heat maps generated for a sensor 120 response of *E. Coli* cultured in a culture medium at 15 hours—a revolutionary finding since the fastest available methods currently take days. Additionally, the sensor 120 response for CRE versus non-CRE *E. coli* showed a difference that was so dramatic in certain of the sensor dyes 710 in the sensor 120 during a certain time window that it could even be identified with the human eye.

Particularly, this study was performed on 35 *Escherichia coli* samples that included 16 CRE and 19 non-CRE samples that were taken directly from a primary blood culture. The samples will cultured in blood culture liquid media VersaTREK aerobic. The initial inoculum of 10 ml at 16 colony forming units (CFU)/ml done in triplicate. The detector 130 captured an image of the sensor 120 used in this study once every 20 minutes. A Carba-R assay was performed on one replicate of each of the samples. Carba-R is a real time polymerase chain reaction assay for rapid detection and differentiation of genes responsible for carbapenem resistance.

Figure 7:
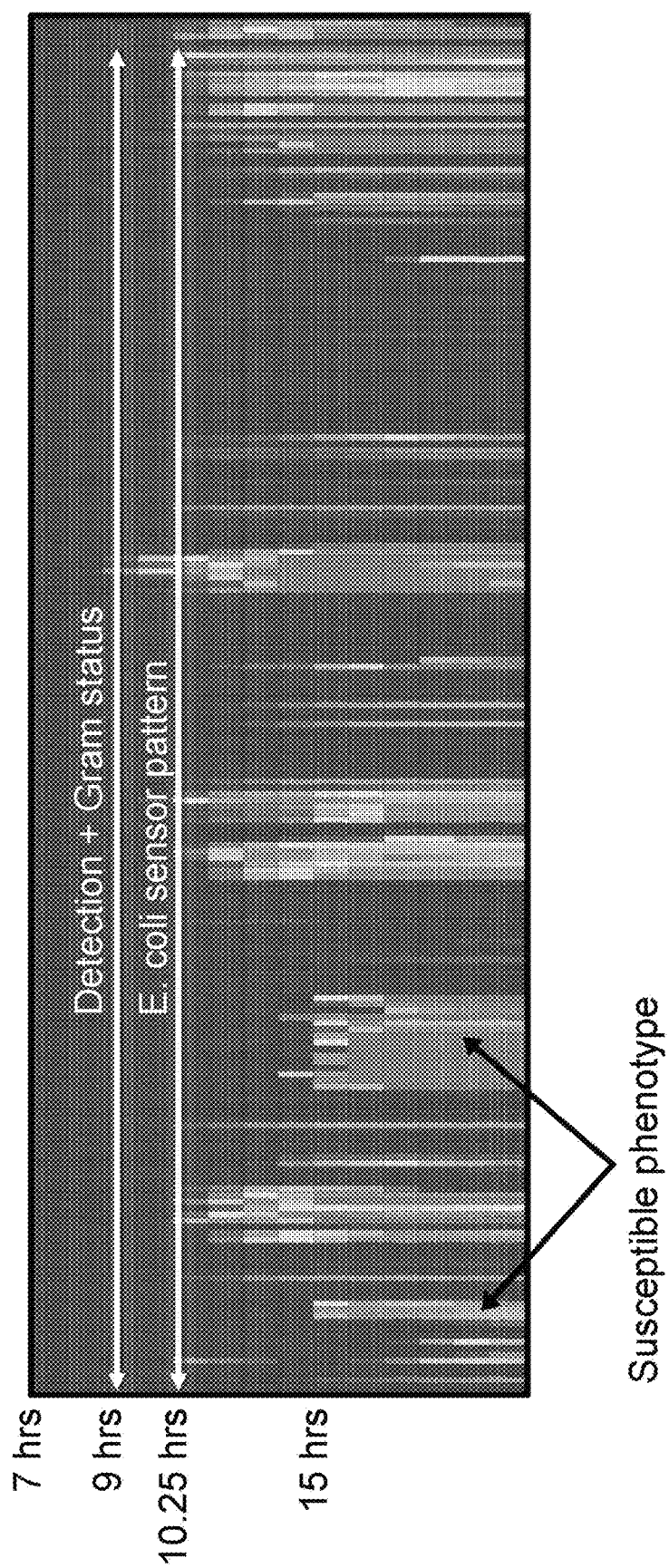
FIG. 7 depicts a heat map of a temporal sensor response showing features indicative of a susceptible phenotype.

FIG. 7 illustrates the results of the study that show a heat map of the progression of a sensor response of *E. coli* over time. As shown, at 9 hours, the system detects growth of the bacteria and at 25 hours the system can detect an *E. coli* sensors pattern. Then, at 15 hours a susceptibility phenotype appears on the heat map that is common to other *E. coli* strains.

Figure 8:
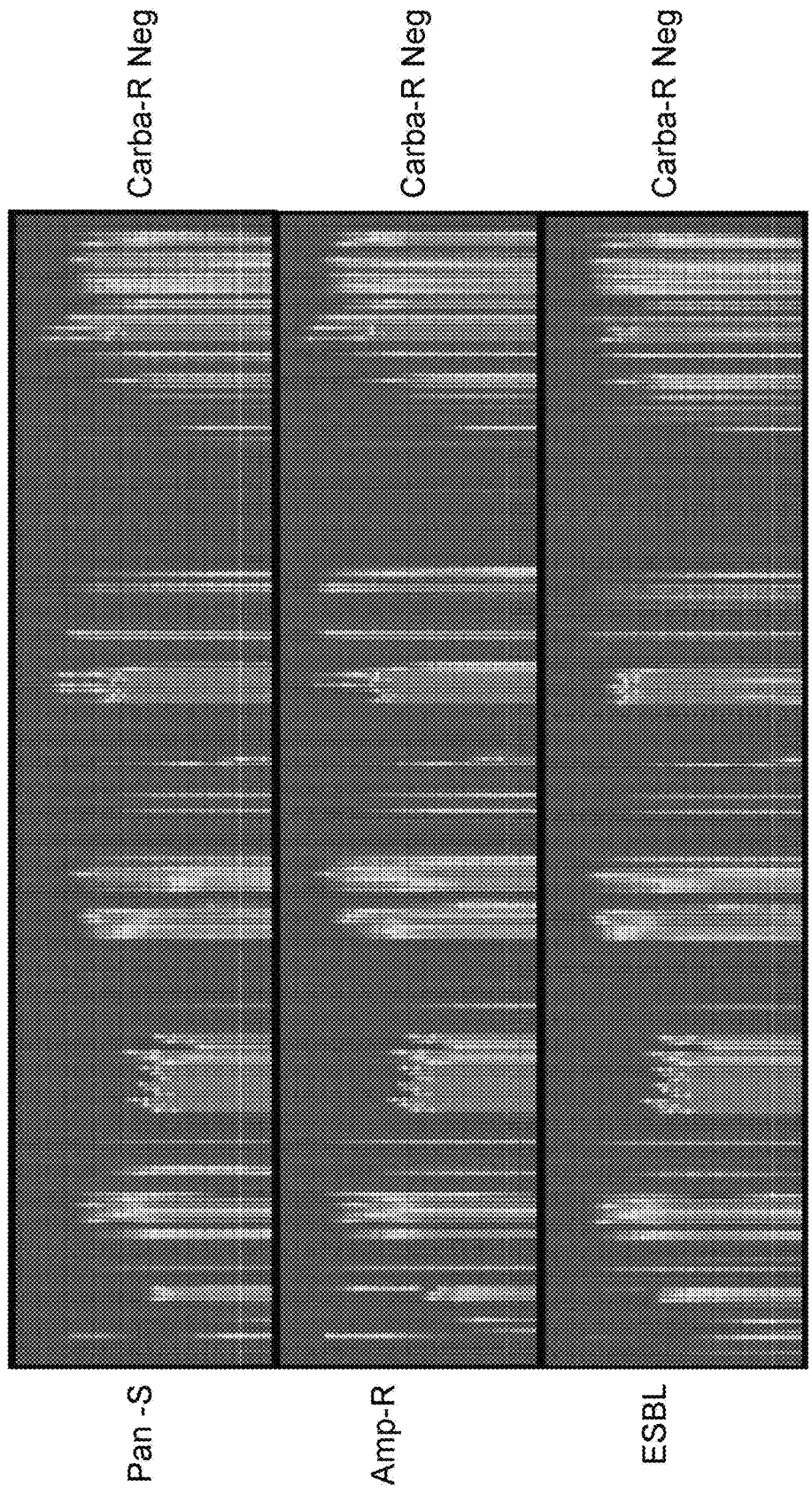
FIG. 8 depicts heat maps of temporal responses of three different strains of *E. coli;*
Figure 9:
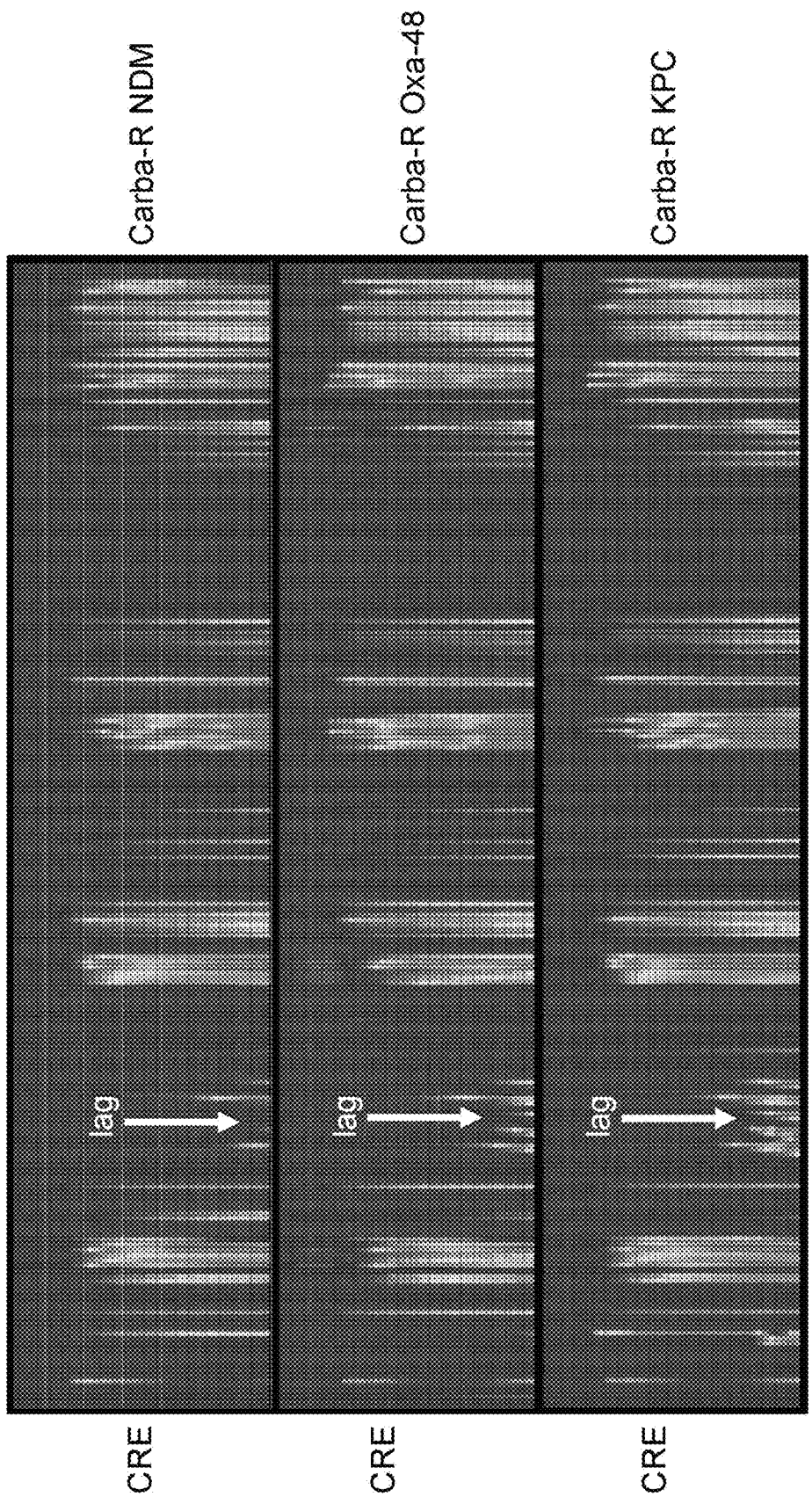
FIG. 9 depicts heat maps of temporal responses of three different strains of *E. coli;*

FIG. 8 illustrates heat maps of carbapenem susceptible *E. coli* strains that all include the feature of certain sensor response that indicates a susceptibility to carbapenem. As illustrated, the Carba-R test was negative for each of these strains. FIG. 9 illustrates heat maps of carbapenem resistant *E. coli*, that all lack the feature that is present in the susceptible strains—accordingly the lack of the feature signifies or indicates that these *E. coli* strains are likely carbapenem resistant. For instance, in FIG. 9, the feature (increased sensor response for certain indicators) that was present as a red patch in the time frame indicated (e.g. starting at 15 hours) that signifies susceptibility, lagged in time quite a bit, and did not appear for hours later. Accordingly, this lack of response on the time window indicated seems to be indicative of a resistance to carbapenem for *E. coli*.

Figure 10:
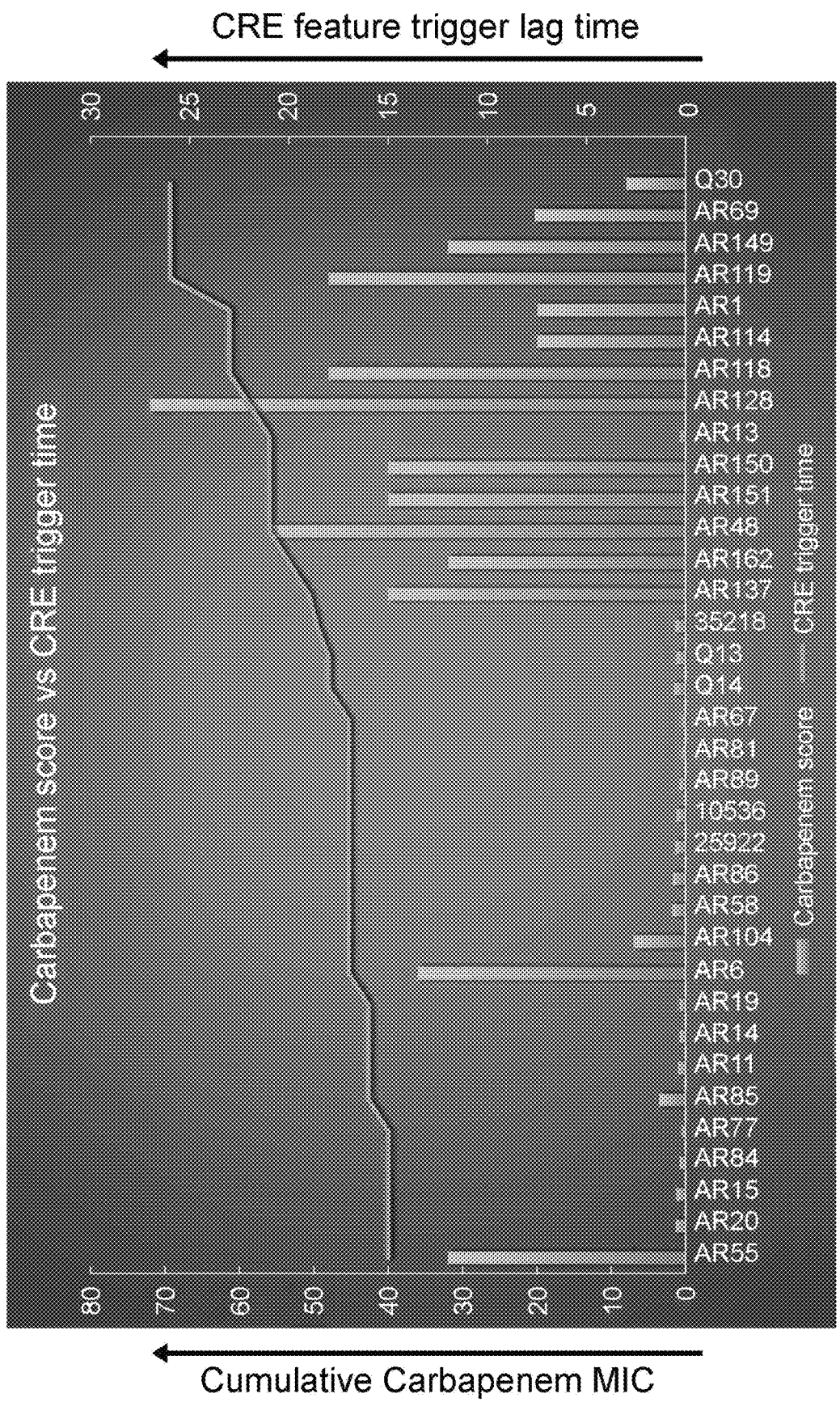
FIG. 10 depicts a line graph showing the time lag of a sensor response for different strains with bar graphs showing the minimum inhibitory concentration of carbapenem.
Figure 11:
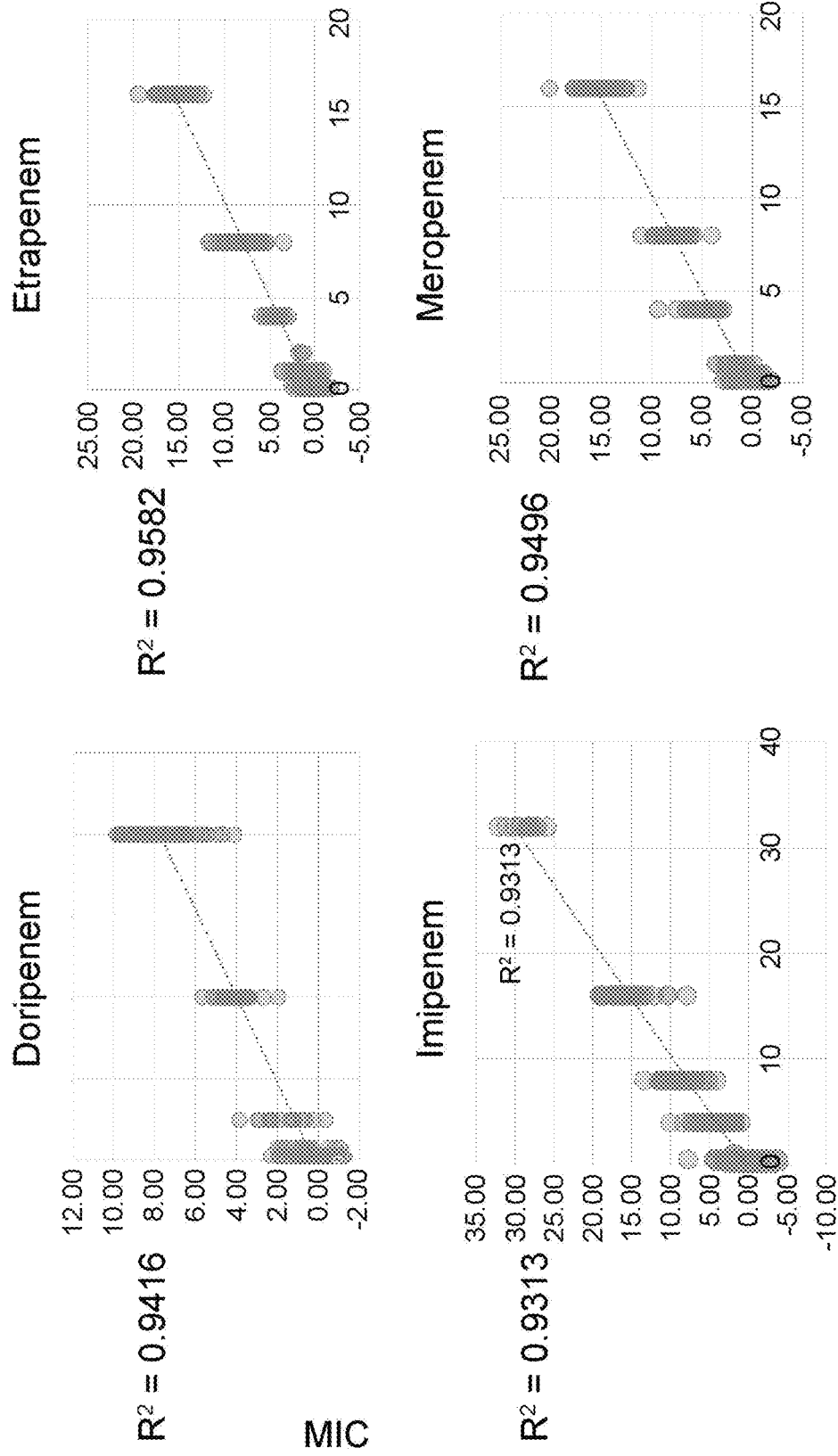
FIG. 11 depicts graphs showing correlations between the sensor lag and the minimum inhibitory concentrations of certain antibiotics.

As illustrated in FIG. 10, *E. coli* carbapenem resistance is predicted by this lag alone with an accuracy of 88% vs. Carba-R accuracy of 97.1%. Additionally, as shown in FIG. 11, the data from FIG. 10 can be used to create a regression model predicting the minimum inhibitory concentration of carbapenem based on the lag of the feature appearing. Accordingly, in some examples, the time lag of a threshold response for certain dyes 710 on the sensor 120 may be processed to determine a minimum inhibitory concentration ("MIC") of carbapenem without performing testing or phenotypic responses of the drug. This is particularly advantageous, because the sensor response 120 without the presence of antibiotics may be enough alone not only to determine drug resistance, particular carbapenem resistance, but to determine a MIC without applying antibiotics in different concentrations which would take many hours longer.

Example 2: Drug Resistant MSSR Signatures

The emergence of Methicillin-resistant strains of *Staphylococcus aureus* ("MRSA") is also a worldwide problem in clinical medicine. People with MRSA are estimated to be 65% more likely to die than people with a non-resistant form of the infection. Accordingly, staph bacteria was tested to determine if signature of drug resistance could be identified.

Figure 12:
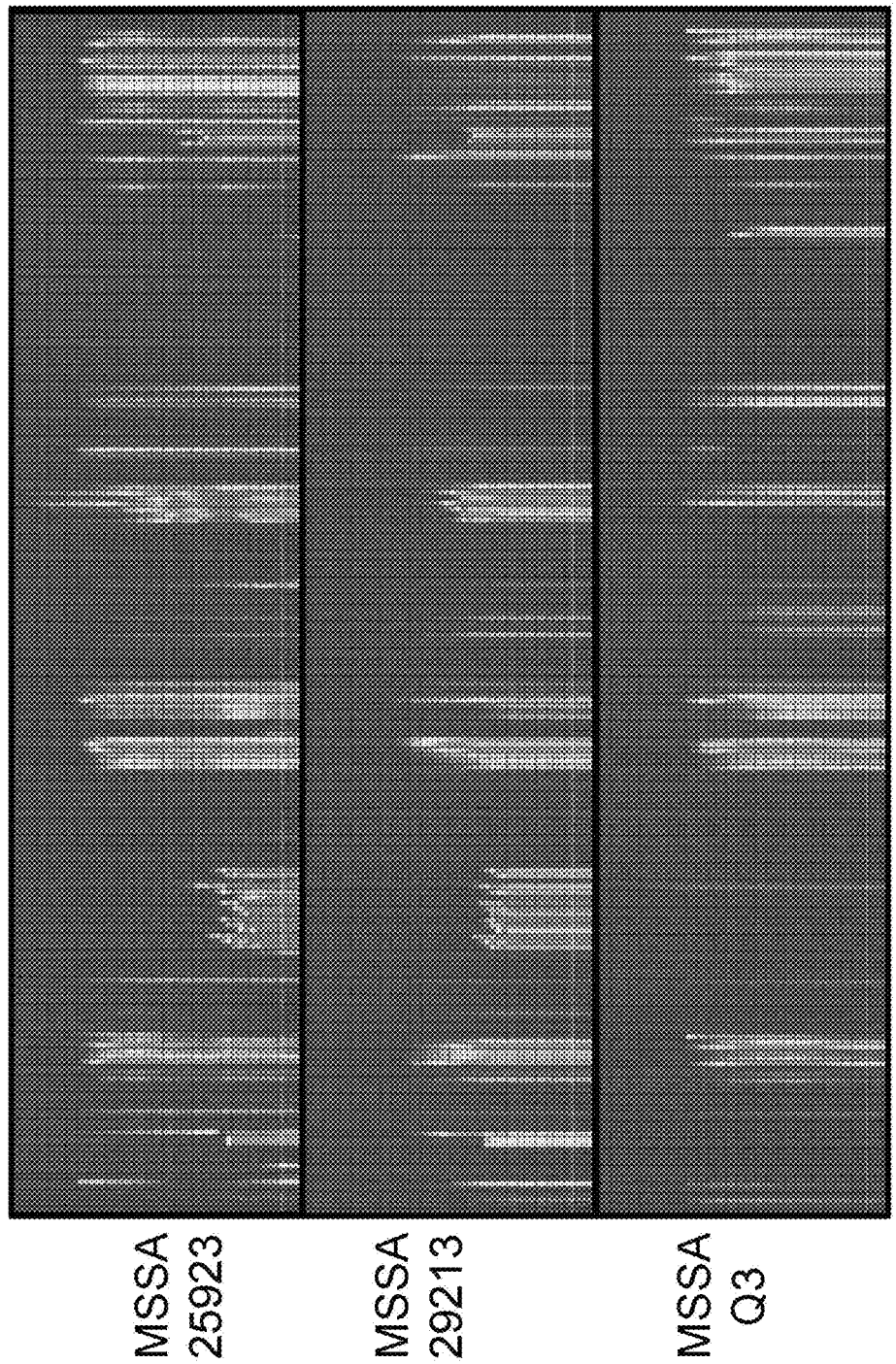
FIG. 12 depicts heat maps of temporal responses of three different strains of *S. aureus;*
Figure 13:
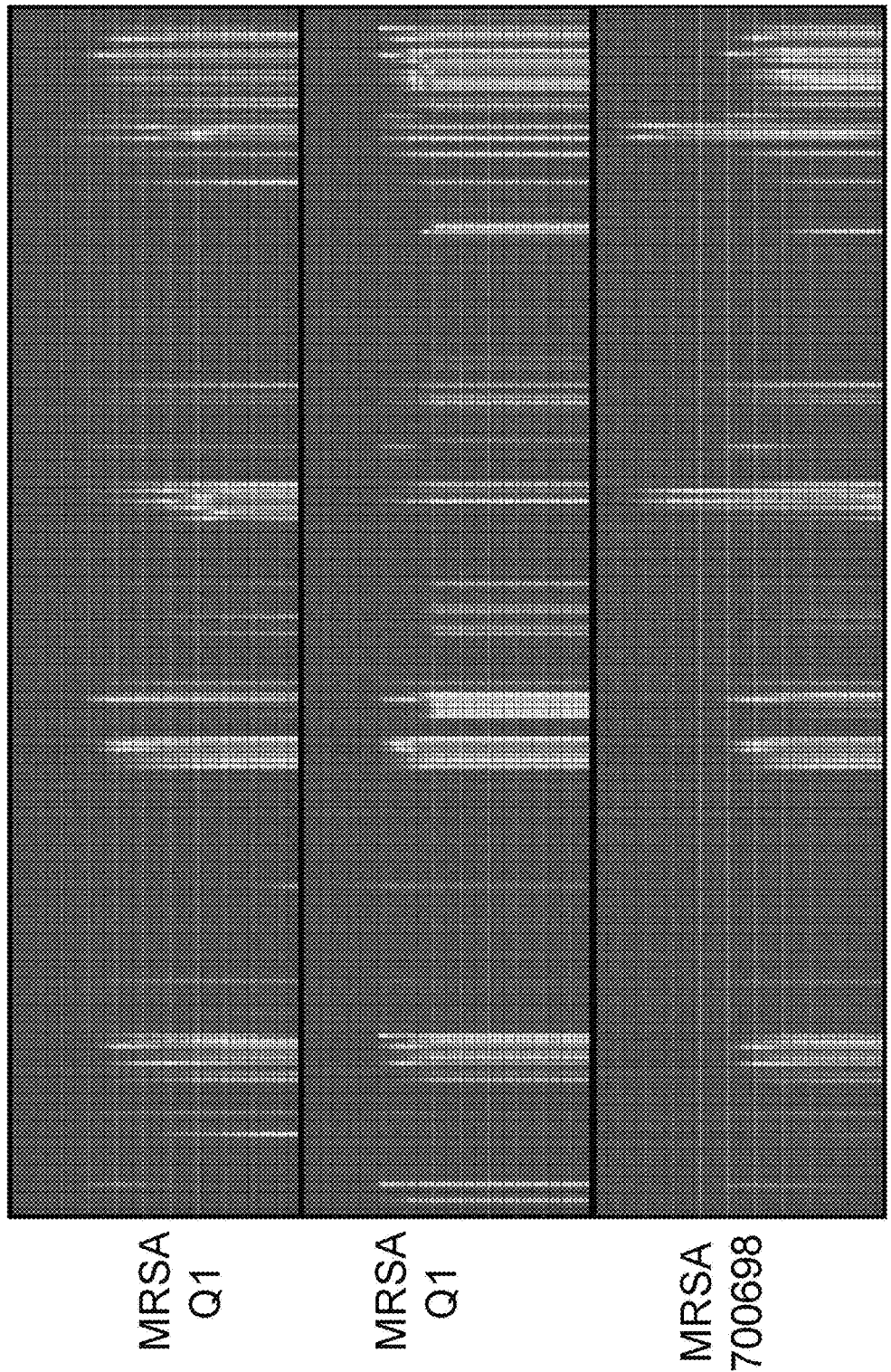
FIG. 13 depicts heat maps of temporal responses of three different strains of *S. aureus;*

Specifically, Methicillin-sensitive *Staphylococcus* ("MSSA") was tested to determine whether it would demonstrate a similar sensor response that indicated drug susceptibility that was independent of strain and compared to Methicillin-resistant *Staphylococcus aureus* ("MRSA"). Accordingly, an analysis of sensor 120 responses comparing Methicillin-sensitive and Methicillin-resistance *S. aureus* was performed to determine if resistance signatures could be identified. FIG. 12 illustrates a heat map showing the sensor 120 response of three Methicillin susceptible strains. Two out of three show a similar response to the susceptible strains of *E. coli*. FIG. 13 illustrates a heat map showing the sensor 120 response of three Methicillin resistant strains. All show a similar response to the resistant strains of *E. coli*. These results are quite interesting, as Methicillin is an antibiotic in the penicillin family of antibiotics—not the Carbapenem family as tested with *E. coli*. Accordingly, the sensor 120 response of Miethillin resistant strains were all similar to the Carbapenem resistant *E. coli*. This shows the disclosed methods for analyzing a sensor response—in particular, a delay in a change in certain indicators or dyes 710 on the sensor—may be utilized in both different strains and even species of bacteria and other microorganisms. Accordingly, the disclosed detection technique can be utilized to identify microorganisms with drug resistance that have not yet been identified by species or strain. Accordingly, this is a powerful tool as organisms and strains continually evolve at a rapidly increasing rate, and another mechanism is needed to identify drug resistance faster than phenotypically using susceptibility drug concentration testing and more robust than genomic identification.

Example 3: CRE vs CSE Strains of *Klebsiella pneumoniae*

*Klebsiella* is a type of Gram-negative bacteria that can cause different types of healthcare-associated infections, including pneumonia, bloodstream infections, wound or surgical site infections, and meningitis. Increasingly, *Klebsiella* bacteria have developed antimicrobial resistance, including most recently to the class of antibiotics known as carbapenems. Accordingly, identifying and treating these antibiotic resistant infections—particularly in the healthcare setting—is becoming increasingly important.

Therefore, an analysis was performed on carbepenem resistant ("CRE") and sensitive ("CSE") strains of *Klebsiella pneumonia*. The sensor 120 responses of four CSE strains and four CRE strains were compared. In this example, instead of analyzing the indicators or dyes 710 that change most notably for *E. coli* and *S. aureus* in Example 1 and 2, other indicator dyes 710 were examined to see if additional patterns in the responses of those dyes 710 could be identified.

Figure 14A:
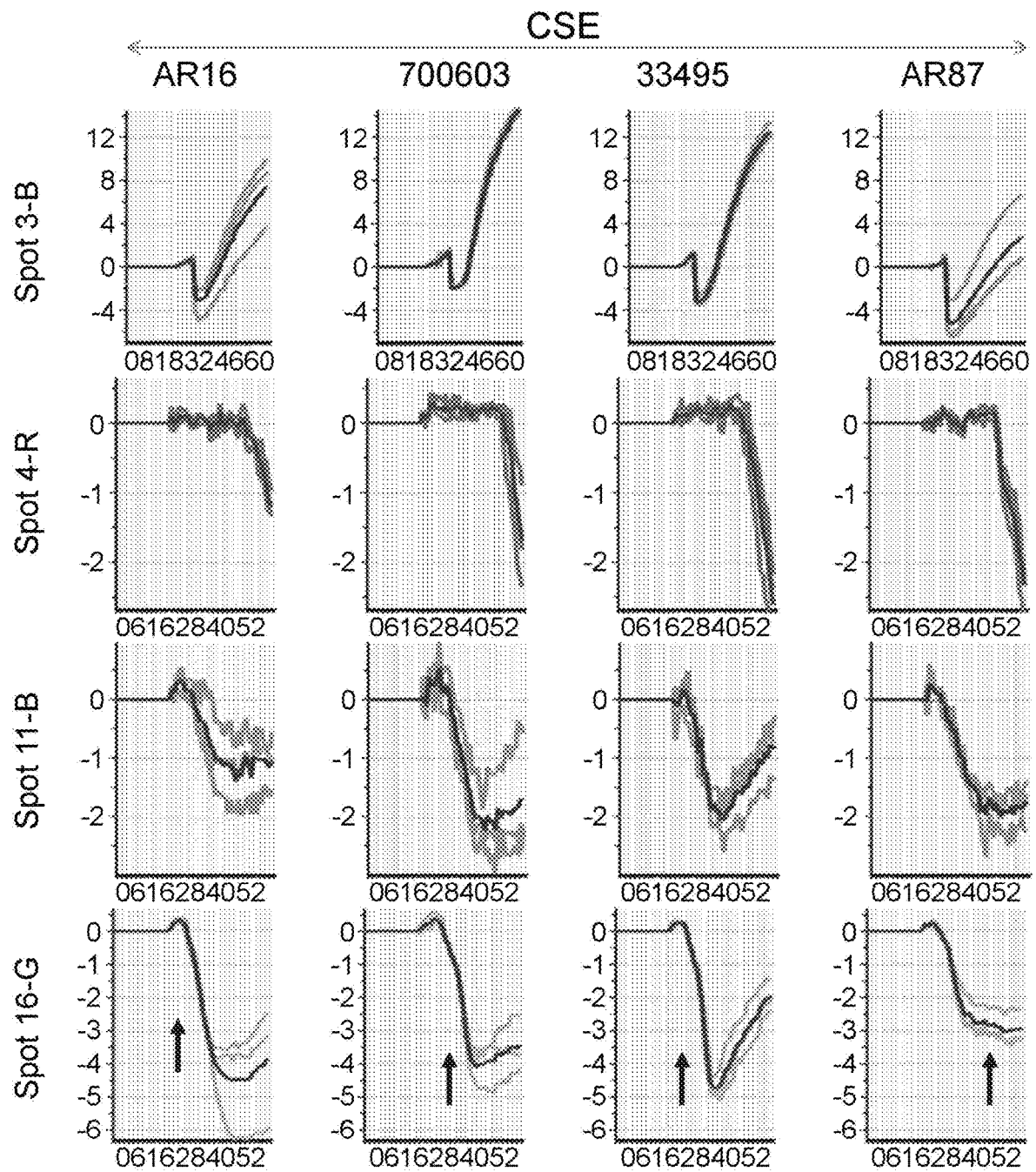
FIGS. 14A-14B depict graphs showing color change responses of individual dyes in one spectrum.
Figure 14B:
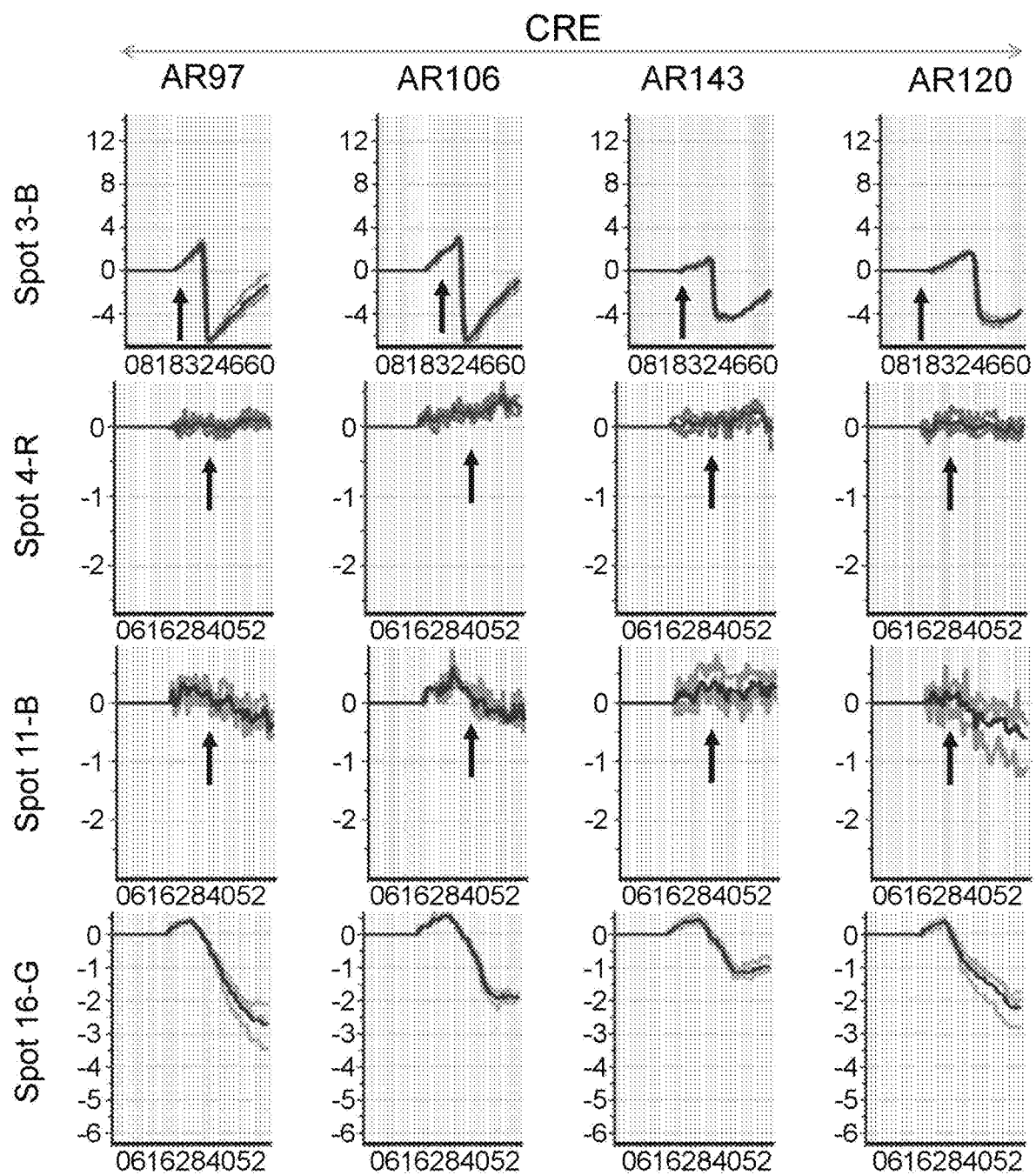
Figure 15:
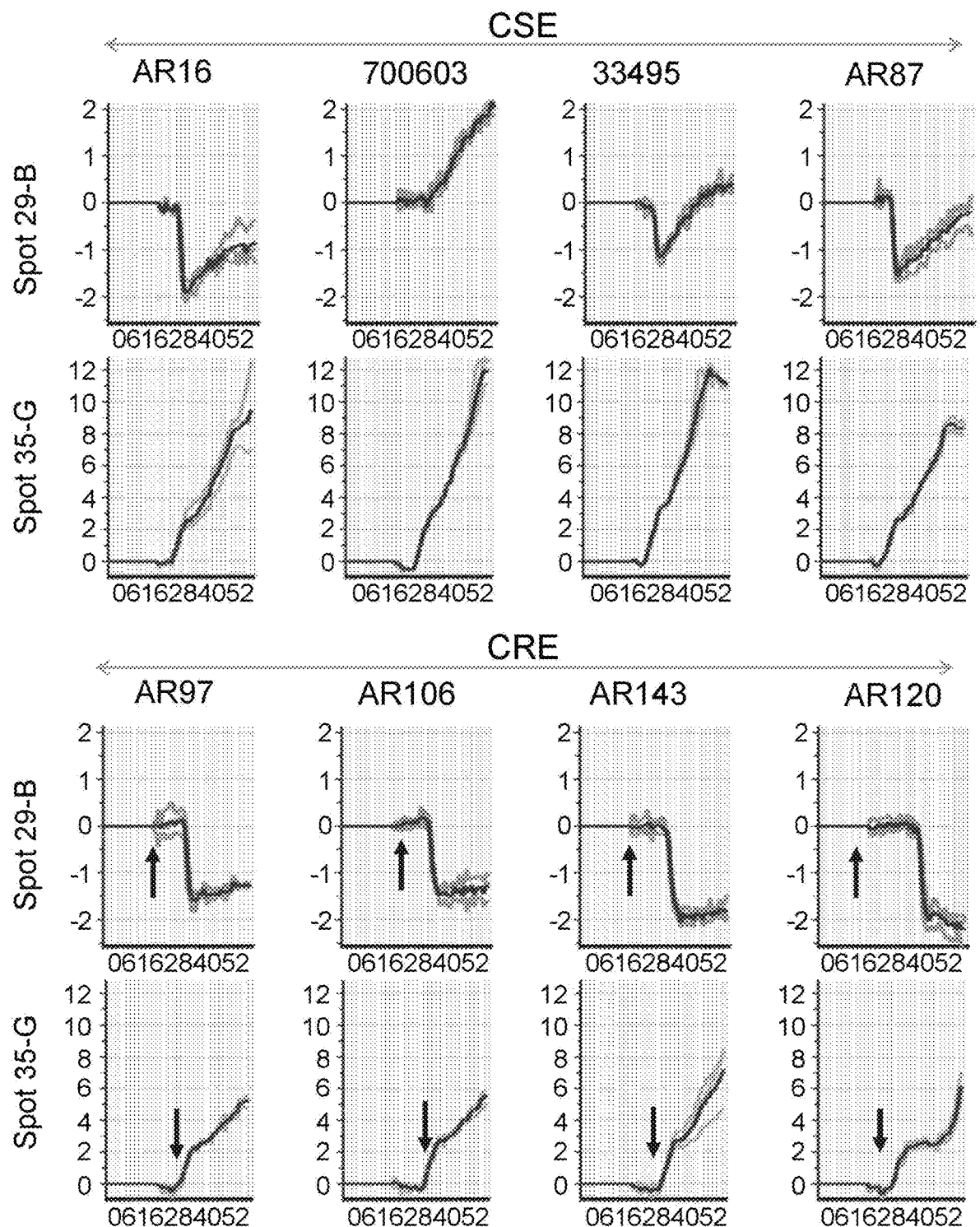
FIG. 15 depicts graphs showing color change responses of individual dyes in one spectrum.

FIGS. 14A-14B and 15 illustrate the results of this comparison. As is immediately apparent from the graphs, very similar patterns are observed between the indicated spots or dyes 710 for the CRE and very similar patterns are observed between the same spots or dyes 710 for CSE strains.

For instance, spot 3-B illustrates a longer upswing before sharply reversing the sensor response. Spot 3-B displays a blue color in the sensor response. Accordingly, algorithms that filter for the steady increase, and then determine when the sensor response sharply decreases, can be implemented. For instance, in some examples, an average slope can be even determined in a short time window, and when that turns negative, a time window of the increase can be determined. If that time window of the increase is larger than a given threshold, in some examples an algorithm can turn a weighted increase in probability that the microorganism is carbapenem resistant.

Spot 4-R illustrates an even more dramatic difference, where the susceptible strains on the left have a response where the red portion of the indicator drops off sharply at a time just before the 40 mark. Spot 4-R displays a red color in the sensor response. As can be seen, the indicators or dyes 710 on the right for the carbapenem resistant strain do not have the same drop off at 40. Accordingly, an algorithm in this case may find an average slope of the change in the color of the red component of spot 4. Once the slope changes to a negative slope below a predetermined threshold, the algorithm and processing equipment can determine that at least one microorganism in the culture may be carbapenem resistant. In some cases, a percentage likelihood of resistance based on the features detected by the graph can be output.

Spot 11B (displaying a blue sensor response) and 16G (displaying a green sensor response), in FIGS. 14A-14B, and spots 29B (displaying a blue sensor response) and 35G (displaying a green sensor response) in FIG. 15 illustrate similar patterns and differences between the resistant and susceptible strains. Accordingly, in some embodiments, a processing step analyzing the rate of change of one or more of the colors of one or more of the dyes 710 may be analyzed. A threshold rate of change in a certain time window can be indicative of a lack or presence of a resistance or a threshold change in a positive or negative direction. In some examples, the signatures in certain time windows may be compared for only certain dyes 710 to determine a resistance. The resistance may be a percentage change of resistance, a resistance to a certain antibiotic or class of antibiotics, or be a mode of resistance, such as an efflux pump.

Example 4: CRE Vs CSE Strains of *E. coli*

The CRE *E. coli* strains show earlier and less variable detection times when compared to the Carbapenem Susceptible *E. coli* (CSE *E. coli*) strains. A method can continuously image and monitor the color changes in the CSA, while the bacteria grow in the blood culture. Color changes are analyzed in real time and a detection event is triggered as soon as the software unequivocally identifies an emerging bacterial volatile signature pattern, which indicates that the blood culture sample is positive for bacterial growth. Gram stain identification happens simultaneously or soon after the bacterial detection, followed by species identification. For example, an *E. coli* sample panel can include 17 CRE strains and the detection time for the strains ranged from 9 hours to 10 hours with the average detection time being 9.65 hours from the time of inoculation. Majority of the CRE strains were detected between 9.3 and 9.7 hours. 40 CSE strains in the panel on the other hand, showed considerably varying detection times ranging from 9 hours to as long as 14.7 hours with the average detection time being 10.2 hours. More than 50% of the CSE strains showed detection times greater than 10 hours. The variation in the detection times for a single strain was no more than 20 minutes (one image capture event) between the technical replicates ran on a single day, and no more than 40 minutes (two image capture events) between the technical replicates ran on different days irrespective of the blood sample used for the experiments. Repeat experiments were performed with the strains with detection times between 11 to 14 hours to confirm that the delayed detection times were consistent in experiments done over a 6 to 8-month period. The CFU per ml of blood in the bottles ranged from 8 CFU/ml to 18 CFU/ml at the beginning of the run over the entire period that the experiments were performed, for all the runs. The detection times had no relationship with the antibiotic susceptibility profiles of the strains as several pan-susceptible strains were detected as late as 12-14 hours.

The CRE *E. coli* strains show a characteristic delay in triggering color change to a specific set of indicators as compared to the CSE *E. coli* strains. The CSA is an array of 73 different colorimetric indicators embedded in a sol-gel matrix, which detect and discriminate a wide range of VOC emitted by different bacteria growing in a blood culture medium (Ref). The different indicators represent a carefully formulated combination of dyes to detect changes in pH and polarity, electrophilic analytes, redox reactions and a host of other chemicals present in the headspace of growing bacteria. These complex mixture of VOC triggers a change in the color of the differentially reactive indicators, which is representative of both the nature of the VOC as well as the rate at which they are released by the growing bacteria in the headspace. There is a clearly differentiable rate of VOC release between the CRE and CSE strains, with CRE strains resulting in a delayed activation of the colorimetric indicators at positions 21-25 in the CSA when compared to the CSE strains. The spots 21-25 belong to a set of colorless indicators that are highly responsive to reduced sulfur compounds along with other volatile families with lesser affinities, and develop dark color on exposure to bacterial volatiles. These indicators showed a marked delay in developing color in the CRE strains as compared to the CSE strains, indicating that the rate of release of reduced sulfur compounds was slower in the CRE strains. This is clearly appreciable when comparing the VOC signal emission patterns of the CRE and CSE strains. A sample analysis can determine the dynamic pattern of the color change that occurs during bacterial growth by analyzing the rate of change of color intensity with time as color change maps, time traces and spatiotemporal heat maps. All the three analysis modalities clearly show the spatiotemporal difference in the emergence of signals at the indicators 21-25 between the CRE and CSE strains. This delayed VOC emission pattern can be called as "*E. coli* Carbapenem susceptibility(Carba-S) feature trigger" and this delay in trigger time can help predict the Carbapenem susceptibility of the strains tested.

Calculating the "lag" in the Carba-S feature trigger after the detection of a strain allows prediction of Carbapenem susceptibility in *E. coli* with high accuracy. A prediction paradigm for Carbapenem susceptibility in *E. coli* can be found by calculating the time a strain takes to generate this specific group of volatiles after automated detection occurs in a blood culture system. A real-time emergence pattern of the 21-25 signal can be observed for each strain. The earliest time point at which signals were observed for all the five indicators was considered as the "Carba-S feature trigger time". Calculating the difference between the Carba-S feature trigger time and the detection time for each strain allows estimation of a "trigger lag time" for each strain. A "Carbapenem MIC score" for each strain can be designated, which is the cumulative MIC value for the four Carbapenems for an individual strain. The trigger lag time can be compared with the Carbapenem MIC score for each strain.

A clear relationship exists between the trigger lag time and the Carbapenem MIC score, with the longer trigger lag times corresponding to higher Carbapenem MICs. 76% ($^{13}/_{17}$) CRE strains showed a measurable Carba-S feature trigger lag ranging from 9.3 hours to 16.7 hours with average trigger lag time being ~12 hours. On the other hand, 87.5% ($^{35}/_{40}$) CSE strains showed trigger lag time ranging from as early as 5 hours to less than 9 hours, with average trigger lag of ~7 hours. Based on these observations, a trigger lag time of ≥9.3 hours is an indicator of putative Carbapenem resistance in the *E. coli*. Application of this trigger lag parameter, enables prediction of a Carbapenem susceptibility with a sensitivity and specificity of 76.5% (95% CI 49.7%-92.2%) and 87.5% (95% CI 72.4%-95.3%) respectively for all the 57 strains in a study panel. The accuracy of prediction of Carbapenem susceptibility is 84.21%. Four out of the 17 CRE strains show a trigger lag time less than 9.3 hours and 5 of the 40 CSE strains show trigger lag time greater than 9.3 hours, which did not conform to trigger lag paradigm considerations. When analyzing the growth characteristics of these strains, 3/5 false positive CSE strains grew extremely slowly with detection times between 11 to 13 hours, which results in a delayed trigger of the 21-25 signal for these strains. A single false negative CRE strain can grow extremely fast with very vigorous volatile response resulting in a trigger lag time of 4 hours, which is much earlier than the Carba-S feature trigger time of all the other strains in a panel. The four strains, or any number of strains, with abnormal growth characteristics can be eliminated. A secondary analysis of the CRE prediction paradigm can be performed on the remaining 53 strains. Eliminating the abnormal four strains increases the sensitivity of a Carbapenem susceptibility prediction paradigm to 81.3% (95% CI 53.7%-95%) and specificity to 94.5% (95% CI 80.5%-99.1%). The accuracy of the assay increased by nearly 6% to 90.6%.

A regression analysis can be performed to estimate the relationship of the response patterns of the indicators in the CSA with the Carbapenem MIC of the CREc strains.

Metabolomic dendrogram can be generated using the spatiotemporal patterns of VOC release and grouping the Carbapenem resistant and susceptible strains into two independent branches. The released VOCs trigger a spatiotemporal pattern of color changes in the sensor array, from which spatiotemporal heat maps can be constructed reflecting the time course of volatile output and strain-specific metabolic fingerprints. The difference between the spatiotemporal heat maps of the different strains can estimate their "relatedness" with respect to their volatile signature profile. To generate metabolomic dendrograms which are reflective of the VOC signature of the strains, a Microreact hierarchical analysis tool can be used. Each indicator response can be normalized to zero mean and unit standard deviation. Strain heatmap differences can compute "distances" between the different strains, enabling the building of metabolic dendrograms. When performing the analysis for the 53 strains (excluding 4 strains with aberrant growth properties), the CSEc and the CREc strains are clearly clustered into two principal independent branches. This underscores their Carbapenem susceptibility specific spatiotemporal pattern of volatile emission in $E.$ $coli$.

A rapid genotypic test can be performed on all the positive blood cultures after the run was over (24 hours) for all the samples, and separately on ten random samples (5 CRE and 5 CSE) right after detection. The assay can detects all the CRE plasmids correctly for 16/17 strains that harbored CRE plasmid. For example, a single CRE strain without any CRE plasmid was detected as negative for CRE by the assay, which was also detected as CSE. All the 40 CSE strains were detected as negative for CRE correctly. There was no difference in performance irrespective of whether the assay was performed at the end of the 24-hour run or right after detection. The sensitivity and specificity values of the Xpert Carba-R assay on the full panel of 57 strains were 94.1% (95% CI 69.2%-99.7%) and 100% (95% CI 89.1%-100%) respectively with an accuracy of 98.2%. 82.3% of the CRE prediction and 87.5% of the CSE prediction matched between the two tests. Calculation of the agreement between the two assays resulted in a Kappa coefficient of 0.68 (95% CI 0.47-0.88) which indicated a "good" agreement between the two tests. Eliminating the 4 strains with aberrant growth characteristics did not result in any changes in the performance characteristics of the Carba-R assay, but increased the Kappa coefficient value to 0.821 (95% CI 0.65-0.99), which indicated a "very good" agreement between the two tests. On this panel of 53 strains the CRE prediction showed an agreement of 87.5% and the CSE prediction showed an agreement of 94.6%. This indicated that a putative Carbapenem susceptibility test from the primary culture showed a high concordance with a definitive genotypic test like the Xpert Carba-R assay.

Therefore, a new paradigm exists for identifying a putative Carbapenem susceptibility signature in $E.$ $coli$ obtained during primary blood culture by monitoring the spatiotemporal pattern of the release of volatile metabolites. The CSA's design enables an accurate detection of the emerging volatile metabolites in the head space of growing bacteria in the blood culture, which is indicative of not only the type of the volatile metabolites, but also the time and the pattern in which they are released during different phases of the bacterial growth. The continuous monitoring of the emerging volatile signals from the growing bacterial headspace allows detection of the differential pattern of the wide variety of volatiles released over time, by observing the selective triggering of specific set of colorimetric indicators formulated to react with the corresponding specific set of volatile molecules. This unique feature of the system, as opposed to simply measuring the growth of the bacteria enables identification of this spatiotemporal difference in emission of reduced sulfur compounds in $E.$ $coli$ strains, which is related to their Carbapenem susceptibility. Monitoring the delayed emission of the reduced sulfur compounds in the CRE strains as compared to the CSE strains enables an accurate prediction of Carbapenem susceptibility in 48/53 $E.$ $coli$ strains with normal growth characteristics.

This is the first report of any diagnostic platform which can generate a prediction about Carbapenem susceptibility in $E.$ $coli$ from primary blood culture, obviating any subsequent susceptibility testing. Elimination of 4 strains with abnormal growth properties from the secondary analysis is based on the time to detection results for multiple reference strains of $E.$ $coli$, for which routine studies have run more than a thousand technical replicates. The present example also eliminated three CSE strains which grew extremely slowly and one CRE strain which grew extremely fast which confounded the trigger lag feature. Out of these 53 strains, the system failed to identify only three CRE strains as CRE since they did not to show the characteristic lag feature as observed in the other CRE strains. One of these CRE strains did not carry any CRE plasmid and was also detected as CRE-negative by the Xpert Carba-R assay. The two CSE strains which were identified as CRE, showed a lag time of 9.3 hours which was same as the minimum threshold trigger lag time for CRE strains. Only 1/13 true positive CRE strains showed a similar trigger lag time of 9.3 hours. In the panel of the 53 $E.$ $coli$ strains, 81% of the CSE strains showed a CRE feature trigger lag below 8 hours and 68% of the CRE strains showed a trigger lag above 10 hours.

The two most common volatile reduced sulfur compound produced by bacteria are hydrogen sulfide and methyl mercaptan. A few studies have reported hydrogen sulfide positive variants of $E.$ $coli$ which were different from typical $E.$ $coli$ strains which do not produce $H_2S$ (Ref). However, these $H_2S$ positive strains are an exception and have been mostly reported in swine fecal matter. This should not have any relevance to a study panel which consists of clinical strains or reference laboratory strains derived from human hosts. No previous studies have shown any relationship between the degree of production of methyl mercaptan in $E.$ $coli$ strains and antibiotic susceptibility. The possibility of a metabolic "cost" in $E.$ $coli$ due to acquiring of Carbapenem resistance, which is reflected as a slower production of reduced sulfur components doesn't seem likely, since the CRE strains on average consistently showed faster detection times than the CSE strains. This phenomenon is also possibly not related to the CRE plasmids acquired by the strains since 3/4 different CRE strains which did not show the characteristic 21-25 signal lag contained NDM or KPC plasmids. The other CRE strains which showed the Carbapenem resistance specific lag also contained NDM or KPC plasmids. The panel in the present exemplary study of CSE strains consisted of ESBL, mono-resistant and several pan-S strains as well. This phenomenon of delayed 21-25 trigger did not seem to be related to acquiring any other resistance inducing plasmids (apart from CRE plasmids) at all since none of the ESBL strains in the study panel showed a CRE feature trigger lag and all the CSE strains showing slower growth or a non-characteristic trigger lag were pan-S strains.

This novel phenomenon, a difference in the rate of release of reduced sulfur compounds, differentiates two distinct genotypic or metabolic clusters of E. coli strains. One class of strains shows a characteristic slower emission rate of reduced sulfur compounds and possibly has a higher propensity of acquiring CRE plasmids; and a second class of strains which release reduced sulfur compounds at a comparatively faster rate, are relatively poor at acquiring resistance inducing plasmids, more specifically CRE plasmids. By studying the spatiotemporal heat maps of the pattern of VOC emission in E. coli growing in blood culture media, it can be found that the reduced sulfur compounds are one of the last group of volatiles which are emitted possibly at the late log to stationary phase, since even the earliest 21-25 signal trigger occur at least 5 hours after detection (~15-16 hours after inoculation). The class of E. coli strains which show a markedly slower reduced sulfur release, appears to have a faster growth rate and a greater probability of acquiring CRE plasmids, while the class of strains with variable growth rates and later detection times appear to show an earlier release of reduced sulfur compounds and have lesser probability of acquiring CRE plasmids. This is attested by the metabolomic dendrogram which clearly results in a dichotomous separation of the E. coli strains into CRE and CSE clusters, which might be reflective of these two classes of strains. The excellent correlation of the prediction with a definitive genotypic test can also be explained by this proposition.

In summary, a highly predictive signature of E. coli CRE phenotype, obtained during primary culture using a CSA-based blood culture system, combines detection and microorganism ID. The Carba-R test performed directly on positive spiked blood culture samples also shows excellent performance on a sample set. The high level of concordance between the phenotypic and the genotypic tests justifies the rationale for the reflex testing of a rapid, labor-free putative resistance determination obtained from the culture CSA fingerprint, to a confirmatory molecular probe based assay like the Carba-R assay. This unique culture system will enable a cost-effect means to characterize strain and predict Carbapenem susceptibility profile of E. coli during primary culture and efficiently link to genomic confirmatory assays like the Carba-R assay and thereby speed the appropriate treatment.

The E. coli strains used in the study were obtained from the Centers for Disease Control and Prevention (CDC) "AR Isolate bank", American Type Culture Collection (ATCC) strain collection bank and clinical strain bank from New York-Presbyterian Hospital (Queens, NY, USA). All the strains from the CDC collection were well characterized with respect to their antibiotic susceptibility and plasmid profile. The entire strain panel in the study consisted of 17 Carbapenem resistant (CR) strains and 40 Carbapenem susceptible (CS) strains. Sixteen out of the seventeen CR strains contained CRE plasmids belonging to NDM (12 strains) and KPC (4 strains) class, with a single strain containing no CRE or ESBL plasmids. The CS strains represented a wide range of antibiotic susceptibility profiles ranging from pan-susceptible, mono-resistant to ESBL, but all were susceptible to Carbapenems (Table?). Glycerol stocks were prepared for each strain and stored at −80° C. until further use.

Sensititre Gram negative GN4F plates (Thermo Fisher Scientific, Waltham, MA) were used to determine the minimal inhibitory concentrations of the Carbapenems Doripenem, Ertapenem, Imipenem and Meropenem. The E. coli strains were streaked out onto blood agar plates (BAP) (Hardy Diagnostics, Santa Maria, CA, USA) at 37° C. and sub-cultured once more before use. Several colonies from the BAP plates were used to generate a 0.5 McFarland standard (~1.5×10$^8$ CFU/ml) in sterile saline. From this suspension 10 µl was transferred to 11 ml of cation adjusted Muellar Hinton Broth (MHB) (Thermo Fisher Scientific, Waltham, MA) for sensititre assay. 50 µl of the MHB suspension was then added to each well of the Sensititre GN4F plate and the plate was incubated for 18-24 hours at 37° C. after covering it with a transparent plate seal. The plate was read using a mirror stand and the MIC values for each antibiotic were recorded. Susceptibility calls for the Carbapenems were made per the 2013 CLSI clinical breakpoint concentration (µg/ml) criteria for Carbapenems for Enterobacteriaceae (Rennie and Jones 2014).

For inoculum preparation, colonies from BAP were suspended in sterile saline, and the turbidity was adjusted to a 0.5 McFarland standard. Each suspension was then serially diluted and plated to confirm the concentration of the bacteria in the suspension. A bacterial suspension of 1 ml corresponding to an appropriate dilution of the McFarland standard, was added to a VersaTREK Redox 1 blood culture bottle (Thermo Fisher Scientific, Waltham, MA, USA), along with 10 ml of whole blood purchased from Innovative Research (Novi, MI, USA), to ensure that the final concentration of the added bacteria was 10 CFU/ml blood in each bottle (100 CFU per bottle). The cap of each blood culture bottle was fitted with a colorimetric sensor array (CSA) inside a proprietary sensor cartridge (Specific Technologies, Mountain View, CA, USA) along with an O-ring and biofilter to ensure the secure placement of the CSA in the bottle caps. The CSA consists of a high-dimensional array of diverse chemically responsive colorimetric indicators embedded in a nanoporous matrix printed on a disposable PVDF membrane, manufactured by Specific Technologies (Ref). Each strain was run in triplicates over a period of two to three different days with at least two different blood samples to ensure the reproducibility of the signals obtained. Each experiment was accompanied by negative control in triplicates which contained blood culture bottles with 10 ml of blood and 1 ml of sterile saline. Upon completion of each run, the positive blood culture medium was plated onto BAP to confirm purity and the cell counts at the end of the run. The negative control samples were also plated to confirm that the culture media as well as the blood were sterile after completion of the run.

The spiked blood cultures were run on a "Spot-On" developmental use only (DUO) blood culture instrument (BCI) (Specific Technologies, Mountain View, CA, USA). The DUO instrument consists of a laptop computer with a custom BCI software for identification of species and two principal components; a flat-bed scanner fitted on the instrument lid and a 12-bottle stirrer for accommodating VersaTREK blood culture bottles. After inoculation of E. coli spiked blood, the VersaTREK bottles were fitted with the sensor cartridge caps, inserted into the instrument and the run was performed inside a 37° C. incubator. Each run was performed using the automated BCI software, during which images of the sensors were automatically collected at a gap of 20 minutes till the termination of the run at 24 hours, to sequentially record the change in the color of the sensor array indicators on exposure to the volatiles emitted by the growing bacteria. The BCI software is programmed to automatically identify the Gram ID followed by the species ID of the bacteria once the blood culture turns positive. At the end of the run, the data was analyzed using the Dataviewer software developed at Specific Technologies. The Dataviewer software allows the visualization of the rate in change of the color intensity of the indicator spots on exposure to VOC as time trace graphs, spatiotemporal heat maps and color change maps. The spatiotemporal pattern of the emergence of the VOC signals with time can be clearly determined for each spot using these three modes of data visualization.

Xpert Carba-R assay was performed on positive blood cultures at the end of the run as well as at detection (for ten random strains). 20 µl of the positive culture was added to the provided sample reagent bottle and vortexed for ten seconds. 1.7 ml of the mix was added to the sample chamber of the Xpert Carba-R cartridge (Cepheid Inc., Sunnyvale, CA) and the assay was performed following the manufacturer's instructions in a GeneXpert IV instrument (Cepheid Inc., Sunnyvale, CA). Automated result outputs were recorded and compared with the prediction done by the CSA system using the antibiotic susceptibility results and plasmid profile (for the CRE strains) as Gold standard.

The sensitivity, specificity and accuracy values of the performance of the Spot-on test and the Xpert Carba-R test as compared to the phenotypic drug susceptibility testing for Carbapenem antibiotics, was calculated at 95% confidence intervals (95% CI). The agreement between the two tests was estimated by calculating the Kappa coefficient using the online Kappa coefficient calculation software to quantify agreement (GraphPad Inc, San Diego, CA, USA).

Dataviewer software has been developed to capture this dynamic change of colors in each indicator across the array as well as the rate of change of the color of each indicator with time which in turn is an efficient measure of the rate at which the growing bacteria release the volatiles in their headspace.

CONCLUSIONS

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The data processing operations described in this specification can be implemented as operations performed by a data processing apparatus on data stored on one or more computer-readable storage devices or received from other sources.

The term "data processing apparatus" encompasses all kinds of apparatus, devices, and machines for processing data, including, by way of example, a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of any computer programs disclosed herein include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, certain implementations and/or portions of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Implementations of certain portions of the subject matter described in this specification can be implemented in a computing system that includes a back-end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer to-peer networks).

Any computing systems disclosed herein can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations may be depicted in the drawings in a particular order, this should not be understood as requiring that such operations be performed in the particular order shown or in sequential order, or that all illustrated operations must be performed in order to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

The invention claimed is:

1. A method comprising:
   culturing a sample containing a microorganism in a medium and in gaseous communication with a colorimetric sensor array, thereby exposing sensors in the colorimetric sensor array to volatile organic compounds produced by the microorganism;
   capturing, by a detector, a rate of color change of the colorimetric sensor array in response to exposing the sensors in the colorimetric sensor array to the volatile organic compounds;
   comparing, by a computer, the rate of color change of the colorimetric sensor array captured from the detector to a stored library of color response patterns; and
   determining, by the computer, that the microorganism lacks resistance to at least one substance based at least in part on the rate of the color change being below a threshold rate of change in the stored library of color response patterns.

2. The method of claim 1, wherein the resistance indicates a multi-drug resistance.

3. The method of claim 1, wherein the resistance is a resistance to a certain antibiotic.

4. The method of claim 1, wherein the resistance is an efflux pump.

5. The method of claim 1, further comprising:
   identifying the microorganism; and
   determining a susceptibility of the microorganism to the at least one substance within 64 hours, within 48 hours, within 36 hours, within 24 hours, within 12 hours, within 10 hours, within 8 hours, within 6 hours, or within 4 hours after identifying the microorganism.

6. The method of claim 1, wherein the resistance is an alternation of a site to which the at least one substance binds.

7. The method of claim 1, wherein the resistance is an alteration of a metabolic pathway.

8. The method of claim 1, wherein the resistance is a modification to a cell envelope of the microorganism.

9. The method of claim 1, further comprising collecting the microorganism from a substrate before culturing the sample containing the microorganism.

10. The method of claim 1, wherein the sample is from a mammal.

11. The method of claim 10, further comprising collecting the sample from the mammal, wherein the sample comprises a gas, a solid, a liquid, or a combination thereof.

12. The method of claim 10, further comprising identifying a susceptible substance to which the microorganism is susceptible based on the lack of resistance of the microorganism to the at least one substance.

13. The method of claim 12, further comprising administering a dose of the susceptible substance to the mammal from which the microorganism was collected, wherein the dose is effective to reduce a population of the microorganism in the mammal.

14. The method of claim 1, wherein the sample comprises blood.

15. The method of claim 1, wherein the detector is selected from the group comprising a spectrophotometer, a scanner and a camera.

16. A method comprising:
    culturing a sample containing a microorganism in a medium and in gaseous communication with a colorimetric sensor array, thereby exposing sensors in the colorimetric sensor array to volatile organic compounds produced by the microorganism;
    capturing, by a detector, a rate of color change of the colorimetric sensor array in response to exposing the sensors in the colorimetric sensor array to the volatile organic compounds;
    comparing, by a computer, the rate of color change of the colorimetric sensor array captured from the detector to a stored library of color response patterns; and
    determining, by the computer, that the microorganism has a resistance to at least one substance based at least in part on the rate of the color change switching directions from a positive rate of change to a negative rate of change.

17. A method comprising:
    culturing a sample containing a microorganism in a medium and in gaseous communication with a colorimetric sensor array, thereby exposing sensors in the colorimetric sensor array to volatile organic compounds produced by the microorganism;
    capturing, by a detector, a delay in triggering of a color change of the colorimetric sensor array in response to exposing the sensors in the colorimetric sensor array to the volatile organic compounds;
    comparing, by a computer, the delay in triggering of the color change of the colorimetric sensor array captured from the detector to a stored library of color response patterns; and
    determining, by the computer, that the microorganism has a resistance to at least one substance based at least in part on the delay captured by the detector.

* * * * *